United States Patent [19]

Murata et al.

[11] Patent Number: 4,822,787

[45] Date of Patent: Apr. 18, 1989

[54] 3-PYRROLIDINYLTHIO-1-AZABICY-CLO(3.2.0)-HEPT-2-ENE-2-CARBOXYLIC ACID COMPOUNDS AND ANTIMICROBIAL ACTIVITY THEREOF

[75] Inventors: Masayoshi Murata, Osaka; Hideo Tsutsumi, Toyonaka; Keiji Matsuda, Takatsuki; Kohji Hattori, Sakai; Takashi Nakajima, Toyonaka, all of Japan

[73] Assignee: Fujisawa Pharmaceutical Co., Ltd., Osaka, Japan

[21] Appl. No.: 116,965

[22] Filed: Nov. 5, 1987

[30] Foreign Application Priority Data

Nov. 24, 1986 [GB] United Kingdom ............... 8628063
Dec. 31, 1986 [GB] United Kingdom ............... 8631081
Apr. 21, 1987 [GB] United Kingdom ............... 8709399
Jul. 17, 1987 [GB] United Kingdom ............... 8716937

[51] Int. Cl.$^4$ ............... A61K 31/33; C07D 205/12
[52] U.S. Cl. ............... 514/210; 540/350
[58] Field of Search ............... 540/350; 514/210

[56] References Cited

U.S. PATENT DOCUMENTS 4,428,960  1/1984  Heck ............... 540/350

FOREIGN PATENT DOCUMENTS 0072710  2/1983  European Pat. Off. ............ 540/350
0102239  3/1984  European Pat. Off. ............ 540/350
0126587  11/1984 European Pat. Off. ............ 540/350
0160391  11/1985 European Pat. Off. ............ 540/350
0182213  5/1986  European Pat. Off. ............ 540/350
59-16892  1/1984  Japan ............... 540/350

Primary Examiner—Mary C. Lee
Assistant Examiner—Robert C. Whittenbaugh
Attorney, Agent, or Firm—Oblon, Fisher, Spivak, McClelland & Maier

[57] ABSTRACT

This invention consists of 3-pyrrolidinylthio-1-azabicyclo[3.2.0]hept-2-ene-2-carboxylic acid compounds and their use as antimicrobial agents in the treatment of infectious diseases.

12 Claims, No Drawings

3-PYRROLIDINYLTHIO-1-AZABICYCLO(3.2.0)-HEPT-2-ENE-2-CARBOXYLIC ACID COMPOUNDS AND ANTIMICROBIAL ACTIVITY THEREOF

The present invention relates to novel 3-pyrrolidinylthio-1-azabicyclo[3.2.0]hept-2-ene-2-carboxylic acid compounds and pharmaceutically acceptable salts thereof.

More particularly, it relates to novel 3-pyrrolidinylthio-1-azabicyclo[3.2.0]hept-2-ene-2-carboxylic acid compounds and pharmaceutically acceptable salts thereof, which have antimicrobial activity, to processes for the preparation thereof, to a pharmaceutical composition comprising the same, and to a use of the same as a medicament and in treatment of infectious diseases in human being or animal.

Accordingly, one object of the present invention is to provide novel 3-pyrrolidinylthio-1-azabicyclo[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid compounds and salts thereof.

A further object of the present invention is to provide a pharmaceutical composition comprising, as an active ingredient, said 3-pyrrolidinylthio-1-azabicyclo[3.2.0]hept-2-ene-2-carboxylic acid compounds and pharmaceutically acceptable salts thereof.

Still further object of the present invention is to provide a use of said 3-pyrrolidinylthio-1-azabicyclo[3.2.0]hept-2-ene-2-carboxylic acid compounds and pharmaceutically acceptable salts thereof as a medicament and in the treatment of infectious diseases by pathogenic microorganisms in human being or animal.

With regard to the status of the art of the present invention, for example, the following compound is known.

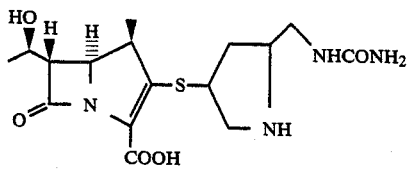

(EP-A-0 182 213)

However antimicrobial spectra of such known compound is restricitve and especially the antimicrobial activity thereof against Gram-negative bacteria such as *P. aeruginosa* is not so potent. Further, the stability against Dehydropeptidase and urinary excretion of such coxpound is insufficient.

Under such a situation, antimicrobial agents having broad antimicrobial spectra, especially having potent antimicrobial activities against Gram-negative bacteria as well as having stability against Dehydropeptidase and good urinary excretion are strongly wanted.

And, as a result of an extensive study, the inventors of the present invention have succeeded in obtaining such superior antimicrobial agents.

The 3-pyrrolidinylthio-1-azabicyclo[3.2.0]hept-2-ene-2-carboxylic acid compounds of this invention are novel and can be represented by the following general formula:

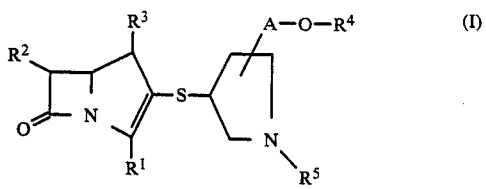

in which
R[1] is carboxy or protected carboxy,
R[2] is hydroxy(lower)alkyl or protected hydroxy(lower)alkyl,
R[3] is hydrogen or lower alkyl,
R[4] is protected or unprotected ureido(lower)alkyl,
R[5] is hydrogen, lower alkanimidoyl or iminoprotective group, and
A is lower alkylene,
and pharmaceutically acceptable salts thereof.

In the object compounds (I) and the intermediary compounds mentioned below, it is to be understood that there may be one or more stereo-isomeric pair(s) such as optical isomers due to asymmetric carbon atom(s), and such isomers are also included within the scope of the present invention.

Suitable pharmaceutically acceptable salts of the object compounds (I) are conventional non-toxic salts and may include a salt with a base such as an inorganic base salt, for example, an alkali metal salt (e.g. sodium salt, potassim salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, dibenzylamine salt, etc.); a salt with an acid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.); an intermolecular quaternary salt, and the like.

According to the present invention, the object compounds (I) and pharmaceutically acceptable salts thereof can be prepared by the processes as illustrated by the following reaction schemes.

Process 1:

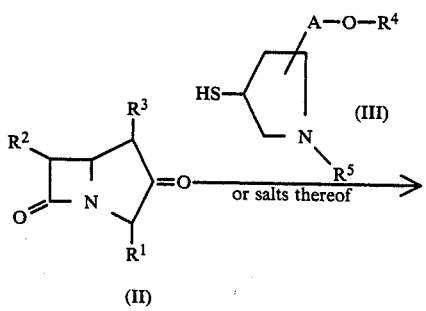

or a reactive derivative
at the oxo group thereof
or salts thereof

Process 2:

(I-a) or salts thereof
→ Elimination reaction of the carboxy-protective group on $R_a^1$ →

(I-b) or salts thereof

Process 3:

(I-c) or salts thereof
→ Elimination reaction of the imino-protective group on $R_a^5$ →

(I-d) or salts thereof

Process 4:

(I-e) or salts thereof
→ Elimination reaction of the hydroxy-protective group on $R_a^2$ →

(I-f) or salts thereof

Process 5:

(I-d) or salts thereof
→ Lower Alkanimidoylating Agent →

(I-g) or salts thereof in which $R^1$, $R^2$, $R^3$, $R^4$, $R^5$ and A are each as defined above, $R_a^1$ is protected carboxy, $R_a^2$ is protected hydroxy(lower)alkyl, $R_b^2$ is hydroxy(lower)alkyl, $R_a^5$ is imino-protective group, and $R_a^5$ is lower alkanimidoyl.

The compound (III) used in the Process 1 is new and can be prepared, for example, by the following methods or a conventional manner.

Method A:

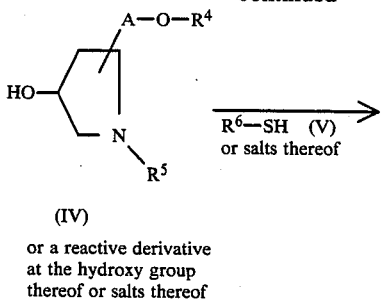

(IV)

or a reactive derivative
at the hydroxy group
thereof or salts thereof

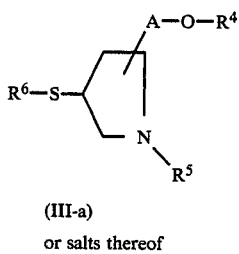

(III-a)

or salts thereof

Method B:

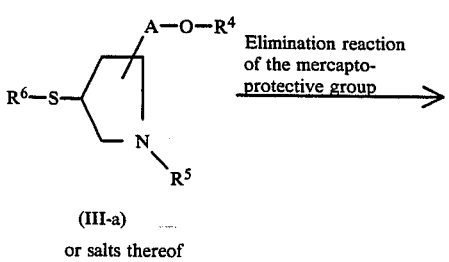

(III-a)

or salts thereof

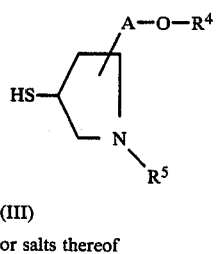

(III)

or salts thereof in which $R^4$, $R^5$ and A are each as defined above, and
$R^6$ is mercapto-protective group.

In the above and subsequent descriptions of the present specification, suitable examples and illustrations of the various definitions which the present invention includes within the scope thereof are explained in detail as follows.

The term "lower" is intended to mean 1 to 6 carbon atoms, unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at lest one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoylox- ymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, propoxycarbonyloxymethyl ester, t-butoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4- methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be phenyl($C_1$-$C_4$)alkoxycarbonyl which may have a nitro group and ($C_{2-C4}$)alkenyloxycarbonyl, and the most preferable one may be 4-nitrobenzyloxycarbonyl and allyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$-$C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; and further ar(lower)alkyl such as mono- or di- or triphenyl(lower)alkyl (e.g. benzyl, benzhydryl, trityl, etc.), etc.;

trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable example of "protected hydroxy(lower)alkyl" thus defined may be {phenyl(or nitrophenyl)($C_1$-$C_4$) alkoxy}carbonyloxy($C_1$-$C_4$)alkyl, {triphenyl($C_1$-$C_4$)alkoxy}($C_1$-$C_4$) alkyl and {tri($C_1$-$C_4$)alkylsilyl}oxy($C_1$-$C_4$)alkyl, and the most preferable one may be 1-t-butyldimethylsilyloxyethyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl.

Suitable "ureido(lower)alkyl" may include straight or branched lower alkyl having ureido group such as ureidomethyl, ureidoethyl, ureidopropyl, 1-(ureidomethyl)ethyl, 1-ureido-1-methylethyl, ureidobutyl, 1,1-dimethyl-2-ureidoethyl, ureidopentyl, ureidohexyl, and the like, in which more preferable example may be ureido($C_1$–$C_4$)alkyl and the most preferable one may be 2-ureidoethyl and 1,1-dimethyl-2-ureidoethyl.

Suitable "protected ureido(lower)alkyl" means aforementioned ureido(lower)alkyl, in which the ureido group is protected by a conventional ureido-protective group such as ar(lower)alkyl which may have suitable substituent(s), for example, mono(or di or tri)phenyl(lower)alkyl (e.g. benzyl, phenethyl, benzhydryl, trityl, etc.), mono(or di)lower alkoxyphenyl(lower)alkyl (e.g. 2,4-dimethoxybenzyl, etc.), bis(lower alkoxyphenyl)(lower)alkyl [e.g. bis(4-methoxyphenyl)methyl, etc.], and the like, in which more preferable one may be phenyl($C_1$–$C_4$)alkyl.

Suitable "lower alkanimidoyl" may be straight or branched one such as formimidoyl, acetimidoyl, propionimidoyl, butyrimidoyl, isovalerimidoyl, pentanimidoyl, hexanimidoyl, and the like, in which more preferable one may be ($C_1$–$C_4$)alkanimidoyl and the most preferable one may be acetimidoyl.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids; and the like.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naththylcarbamoyl, etc.), arenesulfonyl (e.g. benzenesulfonyl, tosyl, etc.), and the like.

The heterocyclic acyl may include heterocycliccarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include aralkanoyl such as phenyl(lower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aryloxyalkanoyl such as phenoxy(lower)alkanoyl (e.g. phenoxyacetyl, phenoxypropionyl, etc.), and the like.

The aliphatic acyl substituted with heterocyclic group(s) may include heterocyclic-alkanoyl such as heterocyclic-(lower)alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, and the like, and preferable acyl having such substituent(s) may be mono(or di or tri)haloalkanoyl (e.g. chloroacetyl, bromoacetyl, dichloroacetyl, trifluoroacetyl, etc.), mono(or di or tri)haloalkoxycarbonyl (e.g. chloromethoxycarbonyl, dichloromethoxycarbonyl, 2,2,2-trichloroethoxycarbonyl, etc.), nitro(or halo or lower alkoxy)aralkoxycarbonyl (e.g. nitrobenzyloxycarbonyl, chlorobenzyloxycarbonyl, methoxybenzyloxycarbonyl, etc.), mono(or di or tri)halo(lower)alkylsulfonyl (e.g. fluoromethylsulfonyl, difluoromethylsulfonyl, trifluoromethylsulfonyl, trichloromethylsulfonyl, etc.), and the like.

More preferable example of "imino-protective group" thus defined may be ($C_2$–$C_4$)alkenyloxycarbonyl and phenyl($C_1$–$C_4$) alkoxycarbonyl which may have a nitro group, and the most preferable one may be allyloxycarbonyl and 4-nitrobenzyloxycarbonyl.

Suitable "lower alkylene" may include straight or branched one such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be methylene.

Suitable "mercapto-protective group" may include acyl as mentioned above, ar(lower)alkyl such as mono- or di- or triphenyl(lower)alkyl (e.g. benzyl, phenethyl, benzhydryl, trityl, etc.), and the like, in which more preferable example may be $C_1$–$C_4$ alkanoyl, aroyl and triphenyl($C_1$–$C_4$)alkyl, and the most preferable one may be acetyl.

The processes for the preparation of the object compounds (I) of the present invention are explained in detail in the following.

(1) Process 1

The compounds (I) or salts thereof can be prepared by reacting the compound (II) or a reactive derivative at the oxo group thereof or salts thereof with the compound (III) or salts thereof.

Suitable salts of the compound (II) may be salts with bases such as those given for the compounds (I).

The reactive derivative at the oxo group of the compound (II) can be represented by the following formula (II'), which is preferably used in this reaction and can be prepared by reacting the compound (II) or salts thereof with an acylating agent.

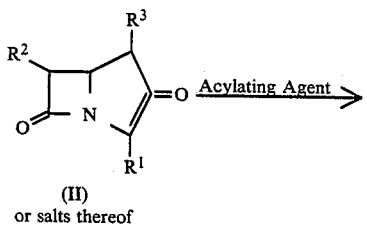

(II)
or salts thereof

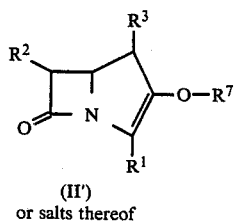

(II')
or salts thereof in which
R$^1$, R$^2$ and R$^3$ are each as defined above, and
R$^7$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compounds (e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.); N,N'-carbonyldiimidazole, N,N'-carbonylbis(2-methylimidazole); keteneimine compounds (e.g. pentamethyleneketene-N-cyclohexylimine, diphenylketene-N-cyclohexylimine); ethoxyacetylene; 1-alkoxy-1-chloroethylene; ethyl polyphosphate; isopropyl polyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like. This acylation reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds [e.g. pyridine, picoline, lutidine, N,N-di(lower)alkylaminopyridine such as N,N-dimethylaminopyridine, etc.], quinoline, N-lower alkylmorphorine (e.g. N-methylmorphorine, etc.), N,N-di(lower)alkylbenzylamine (e.g. N,N-dimethylbenzylamine, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie in tautomeric relation with the 3-hydroxy-7-oxo-1-azabicyclo[3.2.0]hept-2-ene ring system of the following formula (IIB), and accordingly, it is to be understood that both of these ring systems are substantially the same.

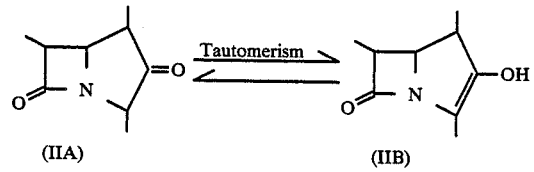

(IIA)  (IIB)

The compound (II') or salts thereof can be used with or without isolation for the subsequent reaction with the compound (III) or salts thereof.

Suitable salts of the compound (III) may be the same as those for the compounds (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process

The compound (I-b) or salts thereof can be prepared by subjecting the compound (I-a) or salts thereof to elimination reaction of the carboxy-protective group on $R_a^1$.

Suitable salts of the compound (I-b) may be the same as those for the compounds (I), and those of the compound (I-a) may be salts with bases such as those given for the compounds (I).

The present reaction is usually carried out by a conventional method such as hydrolysis, reduction, and the like.

(i) Hydrolysis:

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium fluoride (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction:

The reduction method applicable for this elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, palladium hydroxide on carbon, colloidal palladium, palladium on barium sulfate, palladium on barium carbonate, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

This reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite,, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The reaction temperature is not critical and the reaction is usually carried out under from cooling to warming.

The elimination reaction can be selected according to the kind of carboxy-protective group to be eliminated.

The present process includes within the scope thereof a case that the hydroxy- and/or imino-protective group(s) for $R^2$ and/or $R^5$ are removed at the same time during the reaction.

(3) Process 3

The compound (I-d) or salts thereof can be prepared by subjecting the compound (I-c) or salts thereof to elimination reaction of the imino-protective group of $R_a^5$.

Suitable salts of the compound (I-c) may be salts with bases such as those given for the compounds (I), and those of the compound (I-d) may be the same salts with bases and acids for the compounds (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy- and/or hydroxy-protective group(s) for $R^1$ and/or $R^2$ are removed at the same time during the reaction.

(4) Process 4

The compound (I-f) or salts thereof can be prepared by subjecting the compound (I-e) or salts thereof to elimination reaction of the hydroxy-protective group on $R_a{}^2$.

Suitable salts of the compounds (I-e) and (I-f) may be the same as those for the compounds (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in process 2, and therefore are to be referred to said explanation.

In case that the hydroxy-protective group is tri(lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy- and/or imino-protective group(s) for $R^1$ and $R^5$ are removed at the same time during the reaction.

(5) Process 5

The compound (I-g) or salts thereof can be prepared by reacting the compound (I-d) or salts thereof with lower alkanimidoylating agent.

Suitable salts of the compound (I-g) may be the same salts with bases for the compounds (I).

Suitable lower alkanimidoylating agent may be conventional ones which can introduce the lower alkanimidoyl group as mentioned above into the compound (I-d), and said preferable agent may be lower alkyl (lower)alkanimidate (e.g. methyl formimidate, ethyl formimidate, methyl acetimidate, ethyl acetimidate, ethyl propionimidate, ethyl butyrimidate, ethyl isovalerimidate, ethyl pentanimidate, ethyl hexanimidate, etc.), (lower)alkanimidoyl halide (e.g. formimidoyl chloride, formimidoyl bromide, acetimidoyl chloride, acetimidoyl bromide, propionimidoyl chloride, butyrimidoyl chloride, isovalerimidoyl, chloride, pentanimidoyl chloride, hexanimidoyl chloride, etc.), and the like, or an acid addition salt thereof.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 1.

The reaction temperature is not critical, and the reaction is usually carried out under from cooling to starting.

Methods A and B for preparing the new starting compound (III) or salts thereof are explained in detail in the following.

(A) Method A

The compound (III-a) or salts thereof can be prepared by reacting the compound (IV) or a reactive derivative at the hydroxy group thereof or salts thereof with the compound (V) or salts thereof.

Suitable salts of the compounds (III-a), (IV) and (V) may be the same as those for the compound (III).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate and the most preferable one may be methanesulfonate.

The starting compound (IV) or a reactive derivative at the hydroxy group thereof of this method is new and can be prepared by the methods described in the Preparations mentioned below, or by a conventional process.

Preferable example of the compound (V) or salts thereof may be ar(lower)alkanethiol such as mono- or di- or triphenyl(lower)alkanethiol (e.g. phenylmethanethiol, diphenylmethanethiol, triphenylmethanethiol, etc.), thio(lower)alkanoic S-acid (e.g. thioacetic S-acid, etc.), thioarenoic S-acid (e.g. thiobenzoic S-acid, etc.), and the like, or salts thereof, in which more preferable example may be triphenyl($C_1$–$C_4$)alkanethiol, thio($C_1$–$C_4$)alkanoic S-acid and thio($C_6$–$C_{10}$)arenoic S-acid, or salts thereof, and the most preferable one may be thioacetic S-acid or a potassium salt thereof.

The starting compound (IV) of the present reaction is preferably used in a form of its reactive derivative at the hydroxy group, and in such a case, this reaction is usually carried out in the presence of an organic or inorganic base such as those exemplified in the explanation of Process 1.

In case that suitable example of compound (V) may be thio(lower)alkanoic S-acid or thioarenoic S-acid, this reaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercapto-protective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object compounds (I), (I-d), (I-f) and (I-g), and the compounds (III) and (III-a) obtained according to the Processes 1 to 5, and Methods A and B as explained above can be isolated and purified in a conventional manner, for example, extraction, precipitation, fractional crystallization, recrystallization, chromatography, and the like.

In the present invention, the object compounds (I) possessing more potent antimicrobial activity can be represented by the following formula:

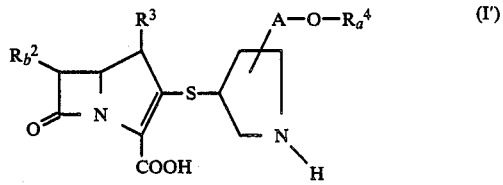

in which
$R_b^2$, $R^3$ and A are each as defined above, and
$R_a^4$ is ureido(lower)alkyl, and
pharmaceutically acceptable salts thereof.

Particularly, the compounds (I) possessing the most potent antimicrobial activity can be represented by the following formula:

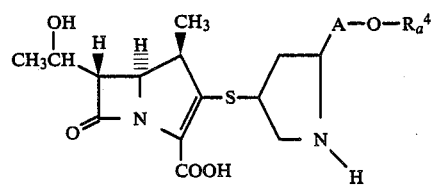

in which $R_a^4$ and A are each as defined above, and pharmaceutically acceptable salts thereof.

The object compounds(I) and pharmaceutically acceptable salts thereof of the present invention exhibit high antimicrobial activity, inhibiting the growth of a wide variety of pathogenic microorganisms including Gram-positive and Gram-negative microorganisms, especially Gram-negative bacteria such as P. aeruginosa and are useful as antimicrobial agents.

Further, the object compounds(I) and pharmaceutically acceptable salts thereof are very stable against Dehydropeptidase and show high urinary excretion, therefore have high potential for the treatment of various diseases, especially urinary tract infections.

Now, in order to show the usefulness of the object compounds (I), the test data on antimicrobial activity of the representative compound of the object compounds (I) of this invention is shown in the following.

in vitro Antimicrobial Activity

Test Method:

in vitro Antimicrobial Activity was determined by the two-fold agar-plate dilution method as described below.

One loopful of 100-fold dilution of an overnight culture of a test strain in Mueller Hinton broth (Difco) (approximately $10^6$ viable cells per ml) was spot-inoculated on Mueller Hinto agar(*) (Difco) containing graded concentrations of the test compound, and the minimal inhibitory concentration (MIC) was expressed in terms of μg/ml after incubation at 37° C. for 20 hours.

[(*)added 5% horse blood-chocolate agar for the test of H. influenzae]

Test Compounds
(1) (4R,5S,6S)-6-[(1R)-1-hydroxyethyl]-4-methyl-7-oxo-3-[(2S,4S)-2-ureidomethylpyrrolidin-4-yl]thio-1-azabicyclo[3.2.0]hept-2-ene-2-carboxylic acid of EP-A-0 182 213 (hereinafter referred to Reference Compound)
(2) (4R,5S,6S)-6-[(1R)-1-hydroxyethyl]-4-methyl-7-oxo-3-[(2S,4S)-2-{(2-ureidoethyl)oxymethyl}pyrrolidin-4-yl]thio-1-azabicyclo[3.2.0]hept-2-ene-2-carboxylic acid of Examples 7, 8, 9 or 10 (hereinafter referred to Compound of this invention)

Test Results:

| | MIC (μg/ml) | |
|---|---|---|
| Test Strains | Reference Compound | Compound of this invention |
| S. aureus 2496 | 1.56 | 0.05 |
| P. aeruginosa 3036 | 1.56 | 0.39 |
| E. cloacae 3013 | 0.1 | ≦0.025 |
| H. influenzae 58 | 0.78 | 0.1 |

For therapeutic administration, the object compounds (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compounds (I) may vary from and also depend upon the age, conditions of the patient, a kind of diseases, a kind of the compounds (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compounds (I) of the present invention may be used in treating diseases infected by pathogenic microorganisms.

The following Preparations and Examples are given for the purpose of illustrating this invention in more detail.

Preparation 1

To a solution of (2S,4R)-4-hydroxy-2-methoxycarbonyl-1-(4-nitrobenzyloxycarbonyl)pyrrolidine (178 g) in N,N-dimethylformamide (500 ml) were added imidazole (93.9 g) and t-butyldimethylsilyl chloride (93.9 g), and the mixture was stirred at ambient temperature for 14 hours. The reaction mixture was diluted with ethyl acetate (2.0 l) and washed in turn with water and brine, and then dried over magnesium sulfate. Removal of the solvent gave (2S,4R)-4-t-butyldimethylsilyloxy-2-methoxycarbonyl-1-(4-nitrobenzyloxycarbonyl)pyrrolidine (260 g).

$[\alpha]_D^{19}$: −36.2° (C=1.00, CHCl$_3$)
IR (CH$_2$Cl$_2$): 1750, 1710 cm$^{-1}$
NMR (CDCl$_3$, δ):0.08 (6H, s), 0.88 (9H, s), 1.8–2.4 (2H, m), 3.3–3.8 (2H, m), $\left.\begin{array}{l} 3.63 \text{ (s)} \\ 3.72 \text{ (s)} \end{array}\right\}$(3H)

4.3–4.5 (2H, m), 5.20 (1H, q, J=14 Hz), 5.23 (1H, s), 7.42 (2H, dd, J=5, 9 Hz), 8.15 (2H, d, J=9 Hz)

Preparation 2

To a solution of (2S,4R)-4-t-butyldimethylsilyloxy-2-methoxycarbonyl-1-(4-nitrobenzyloxycarbonyl)pyrrolidine (790 g) in ethanol (10.0 l) was added sodium borohydride (208 g) and the mixture was stirred at ambient temperature for 16 hours. The reaction mixture was diluted with ethyl acetate (18 l) and washed with brine (4 times), dried over magnesium sulfate and evaporated in vacuo to give a residue. To the residue was added n-hexane and the resulting precipitate was collected by filtration, and washed with a mixture of diisopropyl ether and n-hexane (1:9 V/V) to give (2S,4R)-4-t-butyl-dimethyl-silyloxy-2-hydroxymethyl-1-(4-nitrobenzyloxycarbyl)pyrrolidine (354 g).
mp: 49°–51° C.
$[\alpha]_D^{19}$: −40.2° (C=1.00, CHCl$_3$)
IR (Nujol): 3400, 3300, 1705, 1670 cm$^{-1}$
NMR (CDCl$_3$, δ): 0.07 (6H, s), 0.87 (9H, s), 1.4–2.1 (2H, m), 3.3–3.8 (4H, m), 3.9–4.5 (2H, m), 5.22 (2H, s), 7.47 (2H, d, J=9 Hz), 8.17 (2H, d, J=9 Hz)

Preparation 3

A mixture of (2S, 4R)-4-t-butyldimethylsilyloxy-2-hydroxymethyl-1-(4-nitrobenzyloxycarbonyl)pyrrolidine (10.0 g), methanol (100 ml) and 20% palladium hydroxide on carbon (0.5 g) was stirred under atmospheric pressure of hydrogen at ambient temperature for 3 hours. The catalyst was filtered off and the filtrate was concentrated under reduced pressure to give (2S,4R)-4-t-butyldimethylsilyloxy-2-hydroxymethyl-pyrrolidine. To a solution of the compound obtained above in a mixture of tetrahydrofuran (100 ml) and water (100 ml) was dropwise added a solution of chloroacetyl chloride (5.0 ml) in tetrahydrofuran (10 ml) under ice-cooling with stirring, keeping the pH between 8–9 with 4N aqueous sodium hydroxide. The mixture was stirred at the same condition for 2 hours and extracted with a mixture of ethyl acetate and tetrahydrofuran (1:1 V/V) (100 ml ×5). The solution was dried over magnesium sulfate and concentrated under reduced pressure to give a syrup. The syrup was subjected to a column chromatography on silica gel (200 g) and eluted with a mixture of methanol and dichloromethane (1:99 V/V) to give (2S,4R)-4-t-butyldimethylsilyloxy-1-chloroacetyl-2-(hydroxymethyl)pyrrolidine (4.22 g).

IR (Neat) : 3400, 1660–1630 cm$^{-1}$
NMR (CDCl$_3$, δ): 1.10 (6H, s), 1.90 (9H, s), 1.5–2.3 (3H, m), 3.3–3.9 (5H, m), 4.03 (2H, s), 4.1–4.5 (3H, m)

Preparation 4

A solution of (2S,4R)-4-t-butyldimethylsilyloxy-1-chloroacetyl-2-(hydroxymethyl)pyrrolidine (4.20 g) in tetrahydrofuran (20 ml) was dropwise added to a suspension of sodium hydride (62.8% in oil suspension) (0.55 g) in tetrahydrofuran (60 ml) at 20°–30° C. and the mixture was stirred at 25°–30° C. for 3 hours. The mixture was concentrated under reduced pressure to give a syrup. A solution of the syrup in ethyl acetate (80 ml) was washed with water (100 ml), dried over magnesium sulfate and concentrated under reduced pressure to give a residue. The residue was subjected to a column chromatography on silica gel (30 g) and eluted with a mixture of methanol and chloroform (1:99 V/V) to give (6S,8R)-8-t-butyldimethylsilyoxy-2-oxo-1-aza-4-oxabicyclo[4.3.0]nonane (3.49 g).
mp: 81°–82° C.
IR (Nujol) 1650 cm$^{-1}$
NMR (CDCl$_3$, δ) : 1.10 (6H, s), 1.90 (9H, s), 1.3–1.6 (1H, m), 1.8–2.1 (1H, m), 3.1–3.5 (2H, m), 3.8–4.3 (5H, m), 4.4–4.6 (1H, m)
MS: 256 (M$^+$ − 15), 214

Preparation 5

A suspension of (6S,8R)-8-t-butyldimethylsilyloxy-2-oxo-1-aza-4-oxabicyclo[4.3.0]nonane (1.43 g) in 6N hydrochloric acid (14 ml) was heated for 3 hours under reflux. After cooling, the solution was washed with ethyl acetate (7 ml×2) and concentrated under reduced pressure to give (2S,4R)-2-(carboxymethyloxymethyl)-4-hydroxypyrrolidine hydrochloride.

Preparation 6

To a solution of the compound obtained in Preparation 5 in a mixture of water (30 ml) and tetrahydrofuran (30 ml) was dropwise added a solution of 4-nitrobenzyloxycarbonyl chloride (1.36 g) in tetrahydrofuran (6 ml) under ice-cooling wtth stirring, keeping the pH between 8–9 with 4N aqueous sodium hydroxide. The mixture was stirred under the same condition for 2 hours, adjusted to pH 2.5 with 6N hydrochloric acid and extracted with ethyl acetate (50 ml ×2). The organic solution was combined, washed with brine, dried over magnesium sulfate and concetrated under reduced pressure to give a syrup. The syrup was subjected to a column chromatography on silica gel (20 g) and eluted with a mixture of methanol and chloroform (3:97 V/V) to give (2S,4R)-2-(carboxymethyloxymethyl)-4- hydroxy-1-(4-nitrobenzyloxycarbonyl)pyrrolidine (1.45 g).

IR (Neat): 3600–3300, 1750–1680 cm$^{-1}$

NMR (DMSO-d$_6$, δ): 1.8–2.2 (2H, m), 3.2–3.7 (4H, m), 3.98 (2H, s), 3.9–4.4 (2H, m), 5.20 (2H, s), 7.58 (2H, d, J=8.5 Hz), 8.18 (2H, d, J=8.5 Hz)

Preparation 7

A solution of methanesulfonyl chloride (0.62 ml) in dichloromethane (2 ml) was dropwise added to a solution of (2S,4R)-2-(carboxymethyloxymethyl)-4-hydroxy-1-(4-nitrobenzyloxycarbonyl)pyrrolidine (1.42 g) and triethylamine (1.4 ml) in dichloromethane (14 ml) at 0°–5° C. and the mixture was stirred at the same temperature for 1 hour. The mixture was poured into water (50 ml), adjusted to pH 2.5 with 6N hydrochloric acid and extracted with dichloromethane (50 ml×2). The organic layer was washed with brine, dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-2-(carboxymethyloxymethyl)-4-methanesulfonyloxy-1-(4-nitrobenzyloxycarbonyl)pyrrolidine (1.30 g).

IR (CHCl$_3$): 1750, 1705 cm$^{-1}$

NMR (CDCl$_3$, δ): 2.3–2.5 (2H, m), 3.03 (3H, s), 3.5–4.4 (5H, m), 4.08 (2H, s), 5.22 (2H, s), 5.2–5.4 (1H, m), 5.8–6.2 (1H, m), 7.48 (2H, d, J=8.5 Hz), 8.19 (2H, d, J=8.5 Hz)

Preparation 8

A solution of isobutyl chloroformate (0.60 g) in tetrahydrofuran (1 ml) was dropwise added to a solution of (2S,4R)-2-(carboxymethyloxymethyl)-4-methanesulfonyloxy-1-(4-nitrobenzyloxycarbonyl)pyrrolidine (1.28 g) and triethylamine (0.82 ml) in tetrahydrofuran (13 ml) at −10°~−5° C. and the mixture was stirred at the same temperature for 30 minutes. The mixture was dropwise added to concentrated ammonia water (10 ml) at 0°–5° C. and the solution was stirred at the same temperature for 1 hour. The mixture was poured into water (50 ml) and extracted with chloroform (50 ml). The organic layer was dried over magnesium sulfate and concentrated under reduced pressure to give a syrup. The syrup was subjected to a column chromatogaraphy on silica gel (25 g) and eluted with a mixture of methanol and chloroform (2:98 V/V) to give (2S,4R)-2-(carbamoylmethyloxymethyl)-4-methanesulfonyloxy-1-(4-nitrobenzyloxycarbonyl)pyrrolidine (1.00 g).

IR (Neat): 1710–1670 cm$^{-1}$

NMR (CDCl$_3$, δ): 2.2–2.6 (2H, m), 3.06 (3H, s), 3.5–4.5 (7H, m), 3.98 (2H, s), 5.2–5.5 (1H, m), 5.29 (1H, m), 7.55 (2H, d, J=8.5 Hz), 8.28 (2H, d, J=8.5 Hz)

Preparation 9

To a suspension of sodium borohydride (0.30 g) in tetrahydrofuran (15 ml) was added boron trifluoride etherate (3.5 ml) in a nitrogen stream with stirring at 0°–5° C. The mixture was stirred at the same condition for 30 minutes. To the mixture was added a solution of (2S, 4R)-2-(carbamoylmethyloxymethyl)-4-methanesulfonyloxy-1-(4-nitrobenzyloxycarbonyl)pyrrolidine (1.60 g) in tetrahydrofuran (3 ml) at 0°–5° C. The mixture was stirred at 0°–5° C. for 1 hour and at ambient temperature overnight. Methanol (10 ml) was added to the reaction mixture at 0°–10° C. After 2 hours, insoluble material was filtered off and the filtrate was concentrated under reduced pressure to give a residue. A solution of the residue in a mixture of concentrated hydrochloric acid (3 ml) and methanol (30 ml) was stirred at ambient temperature for 20 hours. The mixture was concentrated under reduced pressure to give (2S,4R)-2-[(2-aminoethyl)oxymethyl]-4-methanesulfonyloxy-1-(4-nitrobenzyloxycarbonyl)pyrrolidine. To a solution of the compound above in a mixture of water (10 ml) and tetrahydrofuran (20 ml) was added a solution of potassium cyanate (1.50 g) in water (5 ml) at 40°–45° C., keeping the pH between 4–5 with concentrated hydrochloric acid. The reaction mixture was extracted with ethyl acetate (50 ml×2). The organic layer was washed with brine, dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-4-methanesulfonyloxy-1-(4-nitrobenzyloxycarbonyl)-2-[(2-ureidoethyl)oxymethyl]pyrrolidine (1.38 g).

IR (CHCl$_3$): 1705–1655 cm$^{-1}$

NMR (CDCl$_3$, δ): 3.07 (3H, s), 5.23 (2H, s), 7.51 (2H, d, J=8.5 Hz), 8.23 (2H, d, J=8.5 Hz)

Preparation 10

A solution of (2S,4R)-4-methanesulfonyloxy-1-(4-nitrobenzyloxycarbonyl)-2-[(2-ureidoethyl)oxymethyl]pyrrolidine (1.37 g) in dimethylformamide (3 ml) was added to a reaction mixture of thioacetic S-acid (0.32 ml) and sodium hydride (62.8% in oil suspension) (0.14 g) in dimethylformamide (7 ml) in a nitrogen stream, and the mixture was heated at 70°–75° C. for 5 hours. The reaction mixture was poured into ice-water (100 ml), extracted with ethyl, acetate (50 ml×2), dried over magnesium sulfate and concentrated under reduced pressure to give a syrup. The syrup was subjected to a column chromatography on silica gel (20 g) and eluted with a mixture of methanol and chloroform (2:98 V/V) to give (2S,4S)-4-acetylthio-1-(4-nitrobenzyloxycarbonyl)-2-[(2-ureidoethyl)oxymethyl]pyrrolidine (1.02 g).

IR (CHCl$_3$): 1710–1655 cm$^{-1}$

NMR (CDCl$_3$, δ): 2.33 (3H, s), 5.20 (2H, s), 7.48 (2H, d, J=8.5 Hz), 8.21 (2H, d, J=8.5 Hz)

Preparation 11

To a solution of (2S,4S)-4-acetylthio-1-(4-nitrobenzyloxycarbonyl)-2-[(2-ureidoethyl)oxymethyl]pyrrolidine (1.01 g) in methanol (20 ml) was added sodium methoxide (28% solution in methanol) (0.5 ml) at −15°–10° C. in a nitrogen stream and the mixture was stirred at the same condition for 1.5 hours. To the mixture was added glacial acetic acid (0.17 ml) at −10°–0° C. The mixture was concentrated under reduced pressure to give a residue. The residue was dissolved in ethyl acetate (50 ml). The solution was washed with water (20 ml), dried over magnesium sulfate and concentrated under reduced pressure to give a syrup. The syrup was subjected to a column chromatography on silica gel (20 g) and eluted with a mixture of methanol and chloroform (2:98 V/V) to give (2S,4S)-4-mercapto-1-(4-nitrobenzyloxycarbonyl)-2-[(2-ureidoethyl)oxymethyl]pyrrolidine (0.74 g).

IR (CHCl$_3$): 1705–1655 cm$^{-1}$

NMR (CDCl$_3$, δ): 5.22 (2H, s), 7.50 (2H, d, J=8.5 Hz), 8.22 (2H, d, J=8.5 Hz)

Preparation 12

To methanol (500 ml) was added conc. sulfuric acid (10 ml) below 30° C. To this solution was added (2S,4R)-1-benzyloxycarbonyl-2-carboxy-4-hydroxypyrrolidine (100 g) and the resulting mixture was heated under reflux for 4 hours. To the mixture was added triethylamine (63 ml) below 10° C. and the mixture was evaporated in vacuo keeping a bath temperature of rotary evaporator below 40° C. to give a syrup. To this syrup were added tetrahydrofuran (100 ml) and toluene (200 ml) successively, and then evaporated in vacuo keeping the bath temperature below 40° C. This procedure was performed once more to give (2S,4R)-1-benzyloxycarbonyl-4-hydroxy-2-methoxycarbonylpyrrolidine. The compound obtained above was dissolved in a mixture of ethyl acetate (1000 ml) and triethylamine (63 ml). To this solution was added dropwise a solution of methanesulfonyl chloride (35 ml) in ethyl acetate (100 ml) at 0°–5° C. over a period of 1.5 hours. This mixture was stirred at the same temprature for additional 30 minutes. This mixture was poured into ice-cold water (1000 ml) with stirring. The organic layer was separated, and washed with 1N hydrochloric acid (1000 ml), saturated aqueous sodium hydrogen carbonate (1000 ml) and brine (1000 ml) successively. This organic layer was evaporated in vacuo keeping the bath temperature below 40° C. to give (2S,4R)-1-benzyloxycarbonyl-4-methanesulfonyloxy-2-methoxycarbonylpyrrolidine. The compound obtained above was dissolved in a of tetrahydrofuran (200 ml) and ethanol (300 ml). To this solution was added sodium borohydride(28.5 g) by three portions below 10° C. and then this mixture was stirred at 25°–30° C. for 2 hours. This mixture was poured into ice-cold water (5000 ml) containing conc. sulfuric acid (92 ml) with vigorous stirring, and the stirring was continued for additional 1 hour to give a white crystal. This crystal was collected by filtration and washed with ice-cold water (500 ml) to give (2S,4R)-1-benzyloxycarbonyl-2-hydroxymethyl-4-methanesulfonyloxypyrrolidine (95.2 g).

IR (CH$_2$Cl$_2$): 3600–3100, 1750–1620 cm$^{-1}$

NMR (CDCl$_3$, δ): 1.82–2.58 (2H, m), 2.92–3.25 (1H, m), 3.00 (3H, s), 3.48–4.00 (4H, m), 4.00–4.41 (1H, m), 5.17 (2H, s), 5.38 (5H, s)

Preparation 13

To a solution of (2S,4R)-1-benzyloxycarbonyl-2-hydroxymethyl-4-methanesulfonyloxypyrrolidine (100 g) and ethyl bromoacetate (100 ml) in tetrahydrofuran (500 ml) was added a solution of potassium t-butoxide (100 g) in tetrahydrofuran (500 ml) in a nitrogen stream at −15° ~ −10° C. for 2 hours and the mixture was stirred at ambient temperature for 3 hours. To the reaction mixture was added 2N aqueous sodium hydroxide (500 ml) at 0°–10° C. and the mixture was stirred at ambient temperature for 18 hours. The organic solvent was evaporated under reduced pressure to give an aqueous solution. To the aqueous solution was added water (500 ml), adjusted to pH 10 with 4N aqueous sodium hydroxide and washed with ethyl acetate (500 ml×2). The aqueous solution was adjusted to pH 4 with concentrated hydrochloric acid and extracted with ethyl acetate (300 ml×2). The organic layer was washed with brine (300 ml), dried over magnesium sulfate and concentrated under reduced pressure to give (2S,4R)-1-benzyloxycarbonyl-2-(carboxymethyloxymethyl)-4-methanesulfonyloxypyrrolidine (94.0 g).

IR (Neat): 3500–3100, 1755–1650 cm$^{-1}$

NMR (CDCl$_3$, δ): 2.99 (3H, s), 4.08 (2H, s), 5.17 (2H, s), 5.2–5.4 (1H, m), 7.37 (5H, s), 8.00 (1H, s)

Preparation 14

A solution of isobutyl chloroformate (9 ml) in tetrahydrofuran (20 ml) was dropwise added to a solution of (2S,4R)-1-benzyloxycarbonyl-2-carboxymethyloxymethyl-4-methanesulfonyloxypyrrolidine (24.85 g) and triethylamine (10.75 ml) in tetrahydrofuran (120 ml) at −10° ~ −5° C. and the mixture was stirred at the same temperature for 30 minutes. The mixture was dropwise added to concentrated ammonia water (250 ml) at 0°–5° C. and the solution was stirred at the same temperature for 30 minutes. The reaction mixture was extracted with ethyl acetate (300 ml). The organic layer was washed with water (200 ml×3), 1N hydrochloric acid (300 ml×2), saturated sodium hydrogen carbonate (300 ml) and brine in turn, dried over magnesium sulfate, and concentrated under reduced pressure to give a syrup. The syrup was subjected to a column chromatography on silica gel (250 g) and eluted with a mixture of methanol and chloroform (2:98 and then 4:96 V/V) to give (2S,4R)-1-benzyloxycarbonyl-2-carbamoylmethyloxymethyl-4-methanesulfonyloxypyrrolidine (15.52 g).

IR (CHCl$_3$): 1710–1660 cm$^{-1}$

Preparation 15

To a suspension of sodium borohydride (3.05 g) in tetrahydrofuran (155 ml) was added boron trifluoride etherate (35.6 ml) in a nitrogen stream with stirring at 0°–5° C. for 30 minutes. The mixture was stirred at the same condition for 30 minutes. To the mixture was added a solution of (2S,4R)-1-benzyloxycarbonyl-2-(carbamoylmethyloxymethyl)-4-methanesulfonyloxypyrrolidine (15.5 g) in tetrahydrofuran (45 ml) at 0°–5° C. for 30 minutes. The reaction mixture was stirred at 0°–5° C. for 30 minutes and at ambient temperature overnight. Ethanol (46.5 ml) was added to the mixture below 10° C. After 2 hours, insoluble material was filtered off and the filtrate was concentrated under reduced pressure to give a residue. A solution of the residue in a mixture of concentrated hydrochloric acid (15.5 ml) and methanol (155 ml) was stirred at ambient temperature overnight. The mixture was concentrated under reduced pressure to give (2S,4R)-2-[(2-aminoethyl)oxymethyl]-1-benzyloxycarbonyl-4-methanesulfonyloxypyrrolidine. To a solution of the compound obtained above in a mixture of water (46.5 ml) and tetrahydrofuran (77.5 ml) was added a solution of potassium cyanate (16.3 g) in water (50 ml) at 40°–50° C., keeping the pH between 4–5 with concentrated hydrochloric acid. The mixture was extracted with ethyl acetate. The organic layer was washed with brine, dried over magnesium sulfate and concentrated under reduced pressure to give (2S,4R)-1-benzyloxycarbonyl-4-methanesulfonyloxy-2-[(2-ureidoethyl)oxymethyl]pyrrolidine (13.28 g).

IR (Neat): 1710–1655 cm$^{-1}$

NMR (CDCl$_3$, δ): 3.03 (3H, 3), 5.16 (2H, s), 7.37 (5H, s)

Preparation 16

A mixture of (2S,4R)-1-benzyloxycarbonyl-4-methanesulfonyloxy-2-[(2-ureidoethyl)oxymethyl]pyrrolidine (13.25 g), concentrated hydrochloric acid (3 ml), methanol (150 ml) and 10% palladium on carbon (0.5 g) was stirred under atmospheric pressure of hydrogen at ambient temperature for 4 hours. The catalyst was filtered off and the filtrate was concentrated under reduced pressure to give (2S,4R)-4-methanesulfonyloxy-2-[(2-ureidoethyl)oxymethyl]pyrrolidine. To a solution of the compound obtained above in a mixture of tetrahydrofuran (100 ml) and water (100 ml) was dropwise added a solution of allyl chloroformate (3.75 ml) in tetrahydrofuran (30 ml) under ice-cooling with stirring, keeping the pH between 8.5–9.5 with 4N aqueous sodium hydroxide. The mixture was stirred at the same condition for 1 hour and extracted with ethyl acetate (100 ml×2). The organic layer was dried over magnesium sulfate and evaporated under reduced pressure to give a syrup. The syrup was subjected to a column chromatography on silica gel (150 g) and eluted with a mixture of methanol and chloroform (2:98 and then 4:96 V/V) to give (2S,4R)-1-allyloxycarbonyl-4-methanesulfonyloxy-2-[(2-ureidoethyl)oxymethyl]pyrrolidine (11.02 g).

IR ($CHCl_3$): 1705–1650 cm$^{-1}$

NMR ($CDCl_3$, δ): 2.2–2.4 (2H, m), 3.06 (3H, s), 5.7–6.2 (1H, m)

Preparation 17-1)

A solution of (2S,4R)-1-allyloxycarbonyl-4-methanesulfonyloxy-2-[(2-ureidoethyl)oxymethyl]pyrrolidine (11.00 g) in dimethylformamide (30 ml) was added to a reaction mixture of thioacetic S-acid (3.05 ml) and sodium hydride (62.8% in oil suspension) (1.4 g) in dimethylformamide (50 ml) in a nitrogen stream and the mixture was heated at 80°–85° C. for 3 hours. The mixture was poured into ice-water (400 ml), extracted with ethyl acetate (150 ml×3), dried over magnesium sulfate and concentrated under reduced pressure to give a syrup. The syrup was subjected to a column chromatography on silica gel (150 g) and eluted with a mixture of methanol and chloroform (2:98 V/V) to give (2S,4S)-4-acetylthio-1-allyloxycarbonyl-2-[(2-ureidoethyl)oxymethyl]pyrrolidine (8.23 g).

IR (Neat): 3500–3100, 1710–1650 cm$^{-1}$

NMR ($CDCl_3$, δ): 2.94 (3H, s)

Preparation 17-2

A solution of (2S,4R)-1-allyloxycarbonyl-4-methanesulfonyloxy-2-[(2-ureidoethyl)oxymethyl]pyrrolidine (1.00 g) and potassium thioacetate (0.48 g) in dimethylformamide (6 ml) was heated at 80°–85° C. for 30 minutes. The mixture was poured into ice-water (30 ml) and extracted with ethyl acetate (12 ml×3). The organic layer was washed with brine (18 ml×2), dried over magnesium sulfate and concentrated under reduced pressure to give a syrup. The syrup was subjected to a column chromatography on silica gel (50 g) and eluted with a mixture of methanol and dichloromethane (5:95 v/v) to give (2S,4S)-4-acetylthio-1-allyloxycarbonyl-2-[(2-ureidoethyl)oxymethyl]pyrrolidine (0.76 g).

IR (neat): 3500–3100, 1710–1650 cm$^{-1}$

NMR ($CDCl_3$, δ): 2.94 (3H, s)

Preparation 18

To a solution of (2S,4S)-4-acetylthio-1-allyloxycarbonyl-2-[(2-ureidoethyl)oxymethyl]pyrrolidine (8.20 g) in methanol (82 ml) was added sodium methoxide (28% solution in methanol) (5.7 ml) at −10°–0° C. in a nitrogen stream and the mixture was stirred at the same condition for 1 hour. To the mixture was added glacial acetic acid (1.9 ml) at −10°–0° C. The mixture was concentrated under reduced pressure to give a residue. The residue was dissolved in ethyl acetate (100 ml). The solution was washed with water (100 ml), dried over magnesium sulfate, and concentrated under reduced pressure to give a syrup. The syrup was subjected to a column chromatography on silica gel (75 g) and eluted with a mixture of methanol and chloroform (2:98 V/V) to give (2S,4S)-1-allyloxycarbonyl-4-mercapto-2-[(2-ureidoethyl)oxymethyl]pyrrolidine (6.89 g)

IR (Neat): 3500–3200, 1710–1640 cm$^{-1}$

Preparation 19

To a solution of (2S,4R)-1-benzyloxycarbonyl-2-carboxy-4-hydroxypyrrolidine (50 g) and triethylamine (63.1 ml) in tetrahydrofuran (250 ml) was dropwise added methanesulfonyl chloride (35.0 ml) with stirring at −5°–0° C. for 2 hours. After stirring for 1 hour, the mixture was poured into ice-water (500 ml) and the solution was adjusted to pH 2 with concentrated hydrochloric acid. The mixture was extracted with ethyl acetate (250 ml). The organic layer was washed in turn with 1N hydrochloric acid (250 ml×2) and brine (250 ml), dried over magnesium sulfate, and evaporated under reduced pressure to give (2S,4R)-1-benzyloxycarbonyl-2-carboxy-4-methanesulfonyloxypyrrolidine (66.21 g).

IR (Neat): 1720–1680 cm$^{-1}$

NMR ($CDCl_3$, δ): 3.01 (3H,s), 5.16 (2H,s), 7.36 (5H,s)

Preparation 20

To a suspension of sodium borohydride (10.7 g) in tetrahydrofuran (600 ml) was added boron trifluoride etherate (43.4 ml) with stirring at 0°–10° C. After stirring for 30 minutes, a solution of (2S,4R)-1-benzyloxycarbonyl-2-carboxy-4-methanesulfonyloxypyrrolidine (66.2 g) in tetrahydrofuran (80 ml) was added to the mixture at 0°–10° C. The mixture was stirred at the same condition for 2 hours. Glacial acetic acid (20 ml) was added to the mixture at 0°–5° C. The reaction mixture was stirred at ambient temperature overnight, poured into ice-water (1 l), extracted with ethyl acetate (400 ml). The organic layer was washed with brine (400 ml), dried over magnesium sulfate and evaporated under reduced pressure to give (2S,4R)-1-benzyloxycarbonyl-2-hydroxymethyl-4-methanesulfonyloxypyrrolidine (56.90 g).

mp: 58°–59° C.

IR (Nujol): 3400, 1700–1675 cm$^{-1}$

NMR ($CDCl_3$, δ): 2.99 (3H, s), 5.16 (2H, s), 7.35 (5H, s)

Preparation 21

A 1.6M solution (4.2 ml) of butyllithium in hexane was added to a solution of (2S,4R)-1-benzyloxycarbonyl-2-hydroxymethyl-4-methanesulfonyloxypyrrolidine (2.00 g) at −30°–20° C. with stirring in a stream of nitrogen and the mixture was stirred at the same temperature for 30 minutes. Ethyl bromoacetate (2.4 ml) was added to the mixture at −30°∼−20° C. and the solution was stirred at 10–15° C. for 3 hours. The solution was poured into 0.1N hydrochloric acid (50 ml) extracted with ethyl acetate (50 ml), dried over magnesium sulfate and concentrated under reduced pressure to give a syrup. The syrup was subjected to a column chromatography on silica gel (20 g) and eluted with chloroform to give (2S,4R)-1-benzyloxycarbonyl-2-(ethoxycarbonylmethyl)oxymethyl-4-methanesulfonyloxypyrrolidine (1.87 g).

IR ($CHCl_3$) : 1740, 1700 cm$^{-1}$

NMR (CDCl$_3$, δ): 1.25 (3H, t, J=7 Hz), 2.98 (3H, s), 3.84 (2H, s), 4.18 (2H, q, J=7 Hz), 5.13 (2H, s), 5.30 (1H, m), 7.32 (5H, s)

Preparation 22

(2S,4R)-1-Benzyloxycarbonyl-2-(ethoxycarbonylmethyl)-oxymethyl-4-methanesulfonyloxypyrrolidine (1.44 g) was dissolved in a 10% solution (30 ml) of ammonia in methanol and the solution was stirred at 25°–30° C. for 12 hours. The solution was concentrated under reduced pressure to give (2S,4R)-1-benzyloxycarbonyl-2-(carbamoylmethyl)oxymethyl-4-methanesulfonyloxypyrrolidine (1.28 g).

IR (CHCl$_3$): 1710–1660 cm$^{-1}$

NMR (CDCl$_3$, δ): 3.0 (3H, s), 3.83 (2H, s), 5.16 (2H, s), 7.36 (5H, s)

Preparation 23

A solution of (6S,8R)-8-t-butyldimethylsilyloxy-2-oxo-1-aza-4-oxabicyclo[4.3.0]nonane (20.0 g) in 6N hydrochloric acid (200 ml) was heated for 3 hours under reflux. After cooling, the solution was washed with ethyl acetate (100 ml) and concentrated under reduced pressure to give (2S,4R)-2-carboxymethyloxymethyl-4-hydroxypyrrolidine. The compound obtained above was dissolved in a mixture of tetrahydrofuran (100 ml) and water (100 ml). To the solution was dropwise added a solution of benzyloxycarbonyl chloride (11.55 ml) in tetrahydrofuran (20 ml) under ice-cooling with stirring, keeping the pH between 8–9 with 4N aqueous sodium hydroxide. The mixture was stirred at the same condition for 1 hour and washed with ethyl acetate (100 ml×2). The aqueous solution was adjusted to pH 2 with 6N hydrochloric acid and ethyl acetate (150 ml) was added thereto. The organic layer was separated, washed with brine, dried over magnesium sulfate and concentrated under reduced pressure to give (2S,4R)-1-benzyloxycarbonyl-2-carboxymethyloxymethyl-4-hydroxypyrrolidine (19.95 g).

IR (CHCl$_3$): 3450–3050, 1750–1660 cm$^{-1}$

NMR (CDCl$_3$, δ): 1.8–2.3 (2H, m), 3.4–3.9 (4H, m), 3.9–4.3 (3H, m), 4.3–4.6 (1H, m), 5.13 (2H, s), 7.34 (5H, s)

Preparation 24

A solution of methanesulfonyl chloride (10 ml) in tetrahydrofuran (20 ml) was dropwise added to a solution of (2S,4R)-1-benzyloxycarbonyl-2-carboxymethyloxymethyl-4-hydroxypyrrolidine (19.95 g) and triethylamine (27 ml) in tetrahydrofuran (200 ml) at −10°∼5° C. and the mixture was stirred at the same temperature for 1 hour. The mixture was poured into water (200 ml), adjusted to pH 2.5 with 6N hydrochloric acid and extracted with ethyl acetate (150 ml×2). The organic layer was washed with brine (200 ml×2), dried over magnesium sulfate and concentrated under reduced pressure to give (2S,4R)-1-benzyloxycarbonyl-2-carboxymethyloxymethyl-4-methanesulfonyloxypyrrolidine (24.85 g).

IR (Neat): 3500–3100, 1755–1650 cm$^{-1}$

Preparation 25

To a solution of (2S,4R)-1-benzyloxycarbonyl-2-carboxymethyloxymethyl-4-methanesulfonyloxypyrrolidine (3.80 g) in benzene (19 ml) was added thionyl chloride (0.90 ml) with stirring at ambient temperature and the mixture was stirred at the same temperature for one hour. To the mixture were added urea (1.80 g) and concentrated sulfuric acid (0.05 ml) successively. The mixture was heated under reflux for 5 hours. The reaction mixture was poured into ice-water (100 ml) and extracted with ethyl acetate (100 ml). The organic layer was dried over magnesium sulfate and concentrated under reduced pressure to give a syrup. The syrup was subjected to a column chromatography on silica gel (100 g) and eluted with a mixture of methanol and chloroform (1:99 V/V) to give (2S,4R)-1-benzyloxycarbonyl-4-methanesulfonyloxy-2-[(ureidocarbonylmethyl)oxymethyl]pyrrolidine (1.85 g).

mp: 120°–122° C.

IR (KBr): 3500–3100, 1725–1685 cm$^{-1}$

NMR (CDCl$_3$, δ): 3.00 (3H, s), 4.04 (2H, s), 5.17 (2H, s), 5.95 (1H, br s), 7.38 (5H, s), 8.03 (1H, br s), 8.85 (1H, br s)

EI MS: 429 (M ), 298, 254

Preparation 26

To a suspension of sodium borohydride (0.1 g) in tetrahydrofuran (10 ml) was added boron trifluoride etherate (0.3 ml) with stirring at 0°–10° C. After 30 minutes, a solution of (2S,4R)-1-benzyloxycarbonyl-4-methanesulfonyloxy-2-[(ureidocarbonylmethyl)oxymethyl]pyrrolidine (0.63 g) in tetrahydrofuran (5 ml) was added to the mixture at 0°–10° C. The mixture was stirred at the same condition for 2 hours and at ambient temperature for 15 hours. Methanol (5 ml) was added to the mixture at 0°–10° C. The mixture was stirred at ambient temperature for 3 hours and concentrated under reduced pressure to give a syrup. The syrup was subjected to a column chromatography on silica gel (25 g) and eluted with a mixture of methanol and chloroform (2:98 V/V) to give (2S,4R)-1-benzyloxycarbonyl-4-methanesulfonyloxy-2-[(2-ureidoethyl)oxymethyl]pyrrolidine (0.24 g).

IR (Neat): 1710–1655 cm$^{-1}$

NMR (CDCl$_3$, δ): 3.03 (3H, s), 5.16 (2H, s), 7.37 (5H, s)

Preparation 27

To a solution of (2S,4R)-1-t-butoxycarbonyl-4-hydroxy-2-methoxycarbonylpyrrolidine (20.0 g) and t-butyldimethylsilyl chloride (18.44 g) in dimethylformamide (60 ml) was added imidazole (11.1 g) under ice-cooling, and the mixture was stirred at 0°–10° C. for 1 hour and then at ambient temperature for 18 hours. The reaction mixture was poured into water (300 ml) and extracted with ethyl acetate (100 ml×3). The combined organic layer was washed with water (200 ml×2) and brine (150 ml) successively, dried over magnesium sulfate, and concentrated under reduced pressure to give a syrup. The syrup was subjected to a column chromatography on silica gel (250 g) to give (2S,4R)-1-t-butoxycarbonyl-4-t-butyldimethylsilyloxy-2-methoxycarbonylpyrrolidine (27.95 g).

IR (Neat): 1750, 1705 cm$^{-1}$

NMR (CDCl$_3$, δ): 0.06 (6H, s), 0.89 (9H, s), 1.42 (9H, s), 3.73 (3H, s)

Preparation 28

To a suspension of lithium aluminum hydride (1.2 g) in tetrahydrofuran (150 ml) was dropwise added a solution of (2S,4R)-1-t-butoxycarbonyl-4-t-butyldimethylsilyloxy-2-methoxycarbonylpyrrolidine (15.0 g) in tetrahydrofuran (30 ml) at 0°–5° C. and the mixture was stirred at the same temperature for 2 hours. To the mixture was dropwise added a solution of water (2 ml) in tetrahydrofuran (5 ml) at 0°–5° C. and the mixture was stirred at ambient temperature for 2 hours. An insoluble material was filtered off and the filtrate was concentrated under reduced pressure to give a syrup. The syrup was subjected to a column chromatography on silica gel (150 g) and eluted with a mixture of methanol and dichloromethane (1:99 V/V) to give (2S,4R)-1-t-butoxycarbonyl-4-t-butyldimethylsilyloxy-2-hydroxymethylpyrrolidine (12.01 g).

IR (Neat): 3400, 1700–1670 cm$^{-1}$

NMR (CDCl$_3$, δ): 0.07 (6H, s), 0.88 (9H, s), 1.51 (9H, s)

Preparation 29

A mixture of (2S,4R)-4-t-butyldimethylsilyloxy-2-hydroxymethyl-1-(4-nitrobenzyloxycarbonyl)pyrrolidine (10.0 g), methanol (100 ml) and 10% palladium on carbon (1.0 g), was stirred in a nitrogen stream at ambient temperature for 3 hours. The catalyst was filtered off and the filtrate was concentrated under reduced pressure to give (2S,4R)-4-t-butyldimethylsilyloxy-2-hydroxymethylpyrrolidine. To a solution of the compound obtained above in tetrahydrofuran (100 ml) was added di-t-butyl dicarbonate (5.60 g) and the mixture was refluxed for 30 minutes. The reaction mixture was concentrated under reduced pressure to give a syrup. The syrup was subjected to a column chromatography on silica gel (160 g) and eluted with chloroform to give (2S,4R)-1-t-butoxycarbonyl-4-t- butyldimethylsilyloxy-2-hydroxymethylpyrrolidine (7.97 g).

IR (Neat): 3400, 1700–1670 cm$^{-1}$

NMR (CDCl$_3$, δ): 0.07 (6H, s), 0.88 (9H, s), 1.51 (9H, s)

Preparation 30

(2S,4R)-1-Benzyloxycarbonyl-4-t-butyldimethylsilyloxy-2-methoxycarbonylpyrrolidine (135.07 g) was obtained by reacting (2S,4R)-1-benzyloxycarbonyl-4-hydroxy-2-methoxycarbonylpyrrolidine (89.70 g) with t-butyldimethylsilyl chloride (72.60 g) and imidazole (43.73 g) successively in substantially the same manner as that of Preparation 1.

IR (Neat): 1750, 1710 cm$^{-1}$

NMR (CDCl$_3$, δ): 0.06 and 0.08 (6H, each s), 0.87 and 0.91 (9H, each s), 3.55 and 3.77 (3H, each s), 5.18 (2H, s), 7.35 (5H, s)

Preparation 31

(2S,4R)-1-Benzyloxycarbonyl-4-t-butyldimethylsilyloxy-2-hydroxymethylpyrrolidine (107.83 g) was obtained by reacting (2S,4R)-1-benzyloxycarbonyl-4-t-butyldimethylsilyloxy- 2-methoxycarbonylpyrrolidine (135.07 g) with sodium borohydride (24.30 g) in substantially the same manner as that of Preparation 2.

IR (Neat): 3400. 1705–1680 cm$^{-1}$

NMR (CDCl$_3$, δ): 0.13 (6H, s), 0.95 (9H, s), 5.25 (2H, s), 7.45 (5H, s)

Preparation 32-1

A solution of (2S,4R)-1-t-butoxycarbonyl-4-t-butyldimethylsilyloxy-2-hydroxymethylpyrrolidine (6.30 g) in tetrahydrofuran (18 ml) was dropwise added to a mixture of methyl bromoacetate (5.4 ml) and sodium hydride (62.8% in oil suspension) (1.46 g) in tetrahydrofuran at 45°–50° C. for 2.5 hours in a nitrogen stream, and the mixture was stirred at 45°–50° C. for 5 hours. To the reaction mixture was added silica gel (15 g) and tetrahydrofuran was evaporated under reduced pressure to give a solid. The solid was subjected to a column chromatography on silica gel (150 g) and eluted with a mixture of hexane and dichloromethane (1:1 V/V) and then with dichloromethane to give a desired compound as a crude syrup (2.09 g). To a solution of the syrup was added sodium methoxide (28% solution in methanol) (0.6 ml) at −10°–0° C. in a nitrogen stream and the mixture was stirred at the same temperature for 1 hour. To the mixture was added glacial acetic acid (0.2 ml) at −10°–0° C. The mixture was concentrated under reduced pressure to give a residue. A solution of the residue in ethyl acetate (20 ml) was washed with water (20 ml) and brine (20 ml) successively, dried over magnesium sulfate, and concentrated under reduced pressure to give (2S,4R)-4-t-butyldimethylsilyloxy-1-t-butoxycarbonyl-2-(methoxycarbonylmetyyloxymethyl)pyrrolidine (0.75 g).

IR (Neat): 1760, 1700 cm$^{-1}$

NMR (CDCl$_3$, δ): 0.06 (6H, m), 0.88 (9H, m), 1.45 (9H, m), 3.73 (3H, s) 4.10 (2H, s),

EI MS: 402, 358

Preparation 32-2

To a solution of (2S,4R)-1-t-butoxycarbonyl-4-t-butyldimethylsilyloxy-2-hydroxymethylpyrrolidine (1.00 g) in tetrahydrofuran (20 ml) was dropwise added a 1.6 M solution of butyllithium in hexane (2 ml) at −40°∼−30° C. in a nitrogen stream and the mixture was stirred at the same temperature for 30 minutes. To the reaction mixture was added ethyl bromoacetate (0.40 ml) at −40°∼−30° C. and the reaction mixture was stirred at −40°∼−30° C. for 30 minutes and then at ambient temperature for 3 hours. The mixture was poured into a mixture of water (50 ml) and ethyl acetate (50 ml). The organic layer was washed with brine (50 ml), dried over magnesium sulfate and concentrated under reduced pressure to give a syrup. The syrup was subjected to a column chromatography on silica gel (20 g) and eluted with chloroform to give (2S,4R)-1-t-butoxycarbonyl-4-t-butyldimethylsilyloxy-2-(ethoxycarbonylmethyloxymethyl)pyrrolidine (0.88 g).

IR (Neat): 1755, 1695 cm$^{-1}$

NMR (CDCl$_3$, δ): 0.03 (6H, s), 0.83 (9H, s), 1.23 (3H, t, J=7 Hz), 1.42 (9H, s), 4.01 (2H, s), 4.16 (2H, q, J=7 Hz)

Preparation 32-3

A mixture of (2S,4R)-4-t-butyldimethylsilyloxy-1-t-butoxycarbonyl-2-(hydroxymethyl)pyrrolidine (0.62 g), 2-bromoacetic acid (0.26 g), 85% potassium hydroxide (0.37 g), and potassium iodide (0.93 g) in t-butyl alcohol (12 ml) was heated at 50° C. for 3 hours. The mixture was poured into water (100 ml), adjusted to pH 4 with 1N hydrochloric acid and saturated with sodium chloride. The aqueous mixture was extracted with three 50 ml portions of ethyl acetate. The organic layer was washed with brine, dried over magnesium sulfate and evaporated. The residue was chromatographed on silica gel (30 g ) eluting with a mixture of methanol and dichloromethane (1:9 V/V) to give (2S,4R)-1-t-butoxycarbonyl-4-t-butyldimethylsilyloxy-2-(carboxymethyloxymethyl)pyrrolidine (0.57 g).

IR (Neat) : 3650–2300, 1700–1650 cm$^{-1}$

NMR (CDCl$_3$, δ): 0.02 (6H, s) 0.83 (9H, s), 1.09–2.13 (2H, m), 1.42 (9H, s), 3.13–3.68 (4H, m), 4.03 (2H, s), 4.07–4.43 (1H, m), 5.01 (1H, br s)

MS: 388 (M$^+$−1)

Preparation 32-4

(2S,4R)-1-Benzyloxycarbonyl-4-t-butyldimethylsilyloxy-2-(ethoxycarbonylmethyloxymethyl)pyrrolidine (0.46 g) was obtained by reacting (2S,4R)-1-benzyloxy- carbonyl-4-t-butyldimethylsilyloxy-2-hydroxymethylpyrrolidine (2.00 g) with a 1.6 M solution of butyllithium in hexane (3.76 ml) and ethyl bromoacetate (0.72 ml) successively in substantially the same manner as that of Preparation 32-2.

NMR (CDCl$_3$, δ): 0.08 (6H, s), 0.88 (9H, s), 1.28 (3H, t, J=7.5 Hz), 4.06 (2H, s), 4.23 (2H, q, J=7.5 Hz), 5.18 (2H, s), 7.38 (5H, s)

Preparation 33-1

A solution of (2S,4R)-1-t-butoxycarbonyl-4-t-butyl dimethylsilyloxy-2-(methoxycarbonylmethyloxymethyl)pyrrolidine (0.75 g) in methanol (21 ml) was saturated with ammonia at ambient temperature and the solution was stirred at the same temperature for 5 hours. The mixture was concentrated under reduced pressure to give a syrup. The syrup was subjected to a column chromatography on silica gel (15 g) and eluted with a mixture of methanol and chloroform (1:99 V/V) to give (2S,4R)-1-t-butoxycarbonyl-4-t-butyldimethylsilyloxy-2-(carbamoylmethyloxymethyl)pyrrolidine (0.61 g).

IR (Neat): 3500-3150, 1705-1675 cm$^{-1}$

NMR (CDCl$_3$, δ): 0.07 (6H, s), 0.88 (9H, s), 1.45 (9H, s), 3.95 (2H, s)

Preparation 33-2

(2S,4R)-1-t-Butoxycarbonyl-4-t-butyldimethylsilyloxy-2-(carbamoylmethyloxymethyl)pyrrolidine is obtained by reacting (2S,4R)-1-t-butoxycarbonyl-4-t-butyldimethylsilyloxy-2-(ethoxycarbonylmethyloxymethyl)pyrrolidine with ammonia in substantially the same manner as that of Preparation 33-1.

IR (Neat): 3500-3150, 1705-1675 cm$^{-1}$

Preparation 33-3

(2S,4R)-1-t-Butoxycarbonyl-4-t-butyldimethylsilyloxy-2-(carbamoylmethyloxymethyl)pyrrolidine is obtained by reacting (2S,4R)-1-t-butoxycarbonyl-4-t-butyldimethylsilyloxy-2-(carboxymethyloxymethyl)pyrrolidine with ammonia in substantially the same manner as that of Preparation 33-1.

IR (Neat): 3500-3150, 1705-1675 cm$^{-1}$

Preparation 33-4

(2S,4R)-1-t-Butoxycarbonyl-4-butyldimethylsilyloxy-2-(carbamoylmethyloxymethyl)pyrrolidine is obtained by reacting (2S,4R)-1-benzyloxycarbonyl-4-t-butyldimethylsilyloxy-2-(ethoxycarbonylmethyloxymethyl)pyrrolidine in substantially the same manner as those of Preparations 29 and 33-1.

IR (Neat): 3500-3150, 1705-1675 cm$^1$

Preparation 34

A solution of (2S,4R)-1-t-butoxycarbonyl-4-t-butyldimethylsilyloxy-2-(carbamoylmethyloxymethyl)pyrrolidine (0.60 g) in a mixture of trifluoroacetic acid (3 ml) and anisole (0.6 ml) was stirred at ambient temperature for 1 hour. The mixture was concentrated under reduced pressure to give (2S,4R)-2-(carbamoylmethyloxymethyl)-4hydroxypyrrolidine. To a solution of the compound obtained above in a mixture of water (20 ml) and tetrahydrofuran (20 ml) was dropwise added a solution of 4-nitrobenzyloxycarbonyl chloride (0.50 g) in tetrahydrofuran (5 ml) under icecooling with stirring, keeping the pH between 8.5–9.5 with 1N aqueous sodium hydroxide. The mixture was stirred at the same condition for 1 hour and extracted with ethyl acetate (50 ml). The organic layer was dried over magnesium sulfate and evaporated under reduced pressure to give a syrup. The syrup was subjected to a column chromatography on silica gel (20 g) and eluted with a mixture of methanol and chloroform (1:99 and then 2:98 V/V) to give (2S,4R)-2-(carbamoylmethyloxymethyl)-4-hydroxy-1-(4-nitrobenzyloxycarbonyl)pyrrolidine (0.32 g).

IR (CHCl$_3$): 3500-3300, 1710-1670 cm$^{-1}$

Preparation 35

(2S,4R)-2-Carbamoylmethyloxymethyl-4-methanesulfonyloxy-1-(4-nitrobenzyloxycarbonyl)pyrrolidine is obtained by reacting (2S,4R)-2-(carbamoylmethyloxy- methyl)-4-hydroxy-1-(4-nitrobenzyloxycarbonyl)pyrrolidine with methanesulfonyl chloride in substantially the same manner as that of Preparation 19.

IR (Neat): 1720-1680 cm$^{-1}$

Preparation 36

(2S,4R)-1-(2-Bromo-2-methylpropionyl)-4-t-butyldimethylsilyloxy-2-(hydroxymethyl)pyrrolidine (3.70 g) was obtained by reacting (2S,4R)-4-t-butyldimethylsilyloxy-2-(hydroxymethyl)pyrrolidine (3.00 g) with 2-bromo-2-methylpropionyl bromide (1.95 g) in substantially the same manner as that of Preparation 3.

mp: 77°–80° C.

IR (Nujol): 1620 cm$^{-1}$

NMR (CDCl$_3$, δ): 0.10 (6H, s), 0.90,(9H, s) 2.00 (6H, s)

Preparation 37

(6S,8R)-8-t-butyldimethylsilyloxy-3,3.dimethyl-2-oxo-1-aza-4-oxabicyclo[4.3.0]nonane (1.18 g) was obtained by reacting (2S,4R)-1-(2-bromo-2-methylpropionyl)-4-t-butyldimethylsilyloxy-2-(hydroxymethyl)-pyrrolidine (3.70 g) with sodium hydride (62.8% in oil suspension) (0.45 g) in substantially the same manner as that of Preparation 4.

mp: 40°–45° C.

IR (Nujol): 1740 cm$^{-1}$

NMR (CDCl$_3$, δ) : 0.02 (6H, s), 0.85 (9H, s), 1.37 (3H, s), 1.43 (3H, s)

Preparation 38

(2S,4R)-2-(1-Carboxy-1-methylethyl)oxymethyl-4-hydroxy-1-(4-nitrobenzyloxycarbonyl)pyrrolidine (0.85 g) was obtained by reacting (6S,8R)-8-t-butyldimethylsilyloxy-3,3-dimethyl-2-oxo-1-aza-4-oxabicyclo[4.3.0-]nonane (1.15 g) with hydrochloric acid and 4-nitrobenzyloxycarbonyl chloride successively in substantially the same manners as those of Preparations 5 and 6.

IR (Neat): 1710-1675 cm$^{-1}$

NMR (CDCl$_3$, δ): 1.39 (3H, s), 1.41 (3H, s), 1.95–2.22 (2H, m), 5.23 (2H, m), 7.48 (2H, d, J=8.5 Hz), 8.19 (2H, d, J=8.5 Hz)

Preparation 39

A solution of methanesulfonyl chloride (0.4 ml) in tetrahydrofuran (2 ml) was dropwise added to a solution of (2S,4R)-2-(1-carboxy-1-methylethyl)oxymethyl-4-hydroxy-1-(4-nitrobenzyloxycarbonyl)pyrrolidine (0.84 g) and triethylamine (1 ml) in tetrahydrofuran (8 ml) at −10°–5° C. and the mixture was stirred at the same condition for 30 minutes. The mixture was dropwise added to a 10% solution (20 ml) of ammonia in ethanol and the mixture was stirred at the same temperature for 1 hour. The mixture was concentrated under reduced pressure to give a residue. The residue was dissolved in ethyl acetate (50 ml), washed with water (50 ml), dried over magnesium sulfate and concentrated under reduced pressure to give a syrup. The syrup was subjected to a column chromatography on silica gel (20 g) and eluted with a mixture of methanol and chloroform (1:99 V/V) to give (2S,4R)-2-(1-carbamoyl-1-methylethyl)oxymethyl-4-methanesulfonyloxy-1-(4-nitrobenzyloxycarbonyl)pyrrolidine (1.01 g).

IR (CHCl$_3$): 1710-1685 cm$^{-1}$

MR (CDCl$_3$, δ): 1.37 (6H, s), 3.05 (3H, s), 5.24 (2H, s), 7.51 (2H, d, J=8.5 Hz), 8.23 (2H, d, J=8.5 Hz)

Preparation 40

(2S,4R)-2-(1,1-Dimethyl-2-ureidoethyl)oxymethyl-4-methanesulfonyloxy-1-(4-nitrobenzyloxycarbonyl)pyrrolidine (3.00 g) was obtained by reacting (2S,4R)-2-(1-carbamoyl-1-methylethyl)oxymethyl-4-methanesulfonyloxy- 1-(4-nitrobenzyloxycarbonyl)pyrrolidine (3.00 g) with a mixture of sodium borohydride (0.66 g) and boron trifluoride etherate (6.25 ml), and then with potassium cyanate (2.65 g) in substantially the same manner as that of Preparation 9.

IR (Neat): 1710-1660, 1605 cm$^{-1}$

NMR (CDCl$_3$, δ): 1.08 (3H, s), 1.10 (3H, s), 3.08 (3H, s)

Preparation 41

(2S,4S)-4-Acetylthio-2-(1,1-dimethyl-2-ureidoethyl)oxymethyl-1-(4-nitrobenzyloxycarbonyl)pyrrolidine (1.42 g) was obtained by reacting (2S,4R)-2-(1,1-dimethyl-2-ureidoethyl)oxymethyl-4-methanesulfonyloxy-1-(4-nitrobenzyloxycarbonyl)pyrrolidine (3.00 g) with thioacetic S-acid in substantially the same manner as that of Preparation 10.

IR (CHCl$_3$): 1710-1670 cm$^{-1}$

NMR (CDCl$_3$, δ): 1.13 (6H, s), 2.35 (3H, s), 5.26 (2H, s), 7.55 (2H, d, J=7.5 Hz), 8.28 (2H, d, J=7.5 Hz)

Preparation 42

(2S,4S)-2-(1,1-Dimethyl-2-ureidoethyl)oxymethyl-4-mercapto-1-(4-nitrobenzyloxycarbonyl)pyrrolidine (0.94 g) was obtained by reacting (2S,4S)-4-acetylthio-2-(1,1-dimethyl-2-ureidoethyl)oxymethyl-1-(4-nitrobenzyloxycarbonyl)pyrrolidine (1.40 g) with 28% sodium methoxide-methanol solution in substantially the same manner as that of Preparation 11 .

IR (CHCl$_3$) : 1705-1650 cm$^{-1}$

NMR (CDCl$_3$, δ): 1.16 (6H, s), 5.20 (2H, s), 7.48 (2H, d, J=7.5 Hz), 8.10 (2H, d, J=7.5 Hz)

Preparation 43

To a solution of allyl (4R)-4-[(2R,3S)-3-{(1R)-1-t-butyldimethylsilyloxyethyl}-4-oxoazetidin-2-yl]-3-oxopentanoate (6.52 g) and triethylamine (6.8 ml) in acetonitrile (50 ml) was added a 1M solution (17 ml) of p-toluenesulfonyl azide in acetonitrile at 0°-5° C. and the mixture was stirred at the same temperature for 2 hours. The mixture was concentrated under reduced pressure to give a residue. The residue was triturated with hexane. The precipitates were filtered off. The filtrate was concentrated under reduced pressure to give a syrup. The syrup was subjected to a column chromatography on silica gel (80 g) and eluted with a mixture of ethyl acetate and hexane (1:9 V/V) to give allyl (4R)-2-diazo-4-[(2R,3S)-3{(1R)-1-t-butyldimetyl-silyloxyethyl}-4-oxoazetidin-2-yl]-3-oxopentanoate (3.78 g).

IR (Neat): 3450-3200, 2150, 1760, 1720, 1650 cm$^{-1}$

NMR (CDCl$_3$, δ):0.07 (6H,s), 0.87 (9H,s)

Example 1

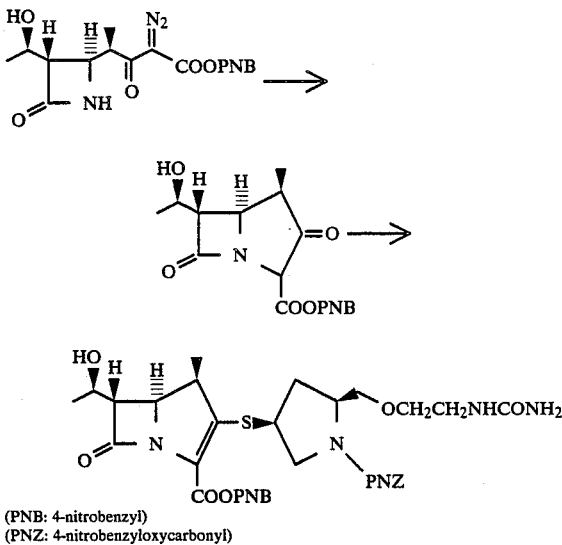

(PNB: 4-nitrobenzyl)
(PNZ: 4-nitrobenzyloxycarbonyl)

To a solution of 4-nitrobenzyl (4R)-2-diazo-4-[(2R,3S)-3-{(1R)-1-hydroxyethyl}-4-oxoazetidin-2-yl]-3-oxopentanoate (0.72 g) in 1,2-dichloroethane (15 ml) was added rhodium(II) acetate (2 mg) under reflux. The mixture was refluxed for 30 minutes under nitrogen atmosphere, cooled and then concentrated under reduced pressure to give 4-nitrobenzyl (4R,5R,6S)-6-[(1R)-1-hydroxyethyl]-4-methyl-3,7-dioxo-1-azabicyclo[3.2.0]-heptane-2-carboxylate. The compound obtained above was dissolved in acetonitrile (15 ml) and N,N-diisopropyl-N-ethylamine (0.39 ml). Diphenyl phosphorochloridate (0.40 ml) was added thereto at −10°∼5° C. in a nitrogen stream, followed by stirring at −10°∼−5° C. for 30 minutes. To the solution were added N,N-diisopropyl-Nethylamine (0.39 ml) and a solution of (2S,4S)-4-mercapto-1-(4-nitrobenzyloxycarbonyl)-2-[(2-ureidoethyl)oxymethyl]pyrrolidine (0.73 g) in acetonitrile (3 ml) at −20° C. successively. The mixture was stirred at the same temperature for 30 minutes and then at 0°-10° C. for 3 hours. The mixture was poured into ethyl acetate (150 ml) and water (100 ml). The organic layer was dried over magnesium sulfate and concentrated under reduced pressure to give a syrup. The syrup was subjected to a column chromatography on silica gel (20 g) eluting with a mixture of acetone and dichloromethane (1:1 V/V) to give 4-nitrobenzyl (4R,5S,6S)-6-[(1R)-1-hydroxyethyl]-4-methyl-3-[(2S,4S)-1-(4-nitrobenzyloxycarbonyl- 2-{(2-ureidoethyl)oxymethyl}pyrrolidin-4-yl]thio-7-oxo-1-azabicyclo[3.2.0]hept-2-ene-2-carboxylate (0.75 g).

IR (CHCl$_3$): 1780-1760, 1710-1650 cm$^{-1}$

Example 2

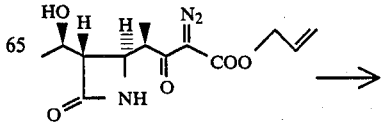

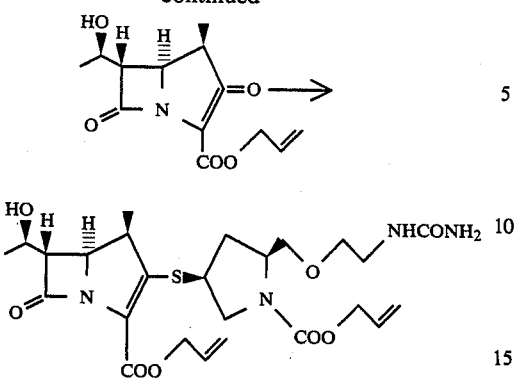

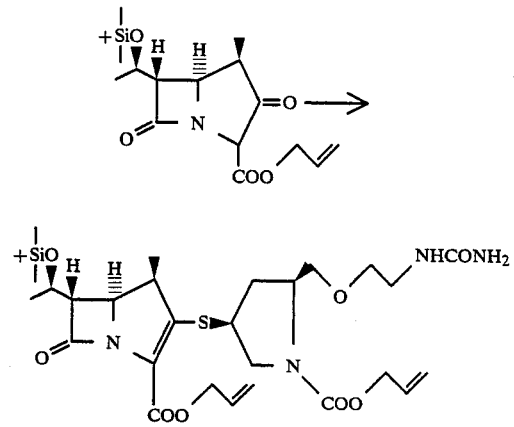

To a solution of allyl (4R)-2-diazo-4-[(2R,3S)-3-{(1R)-1-hydroxyethyl}-4-oxoazetidin-2-yl]-3-oxopentanoate (0.5 g) in dichloromethane (10 ml) was added rhodium(II) octanoate (13.2 mg) under reflux. After refluxing for 20 minutes, to the solution was added rhodium(II) octanoate (13.2 mg). The mixture was refluxed for 40 minutes. The reaction mixture was cooled and evaporated in vacuo to give a residue. The residue was dissolved in anhydrous acetonitrile (10 ml) and then evaporated. This operation was repeated once again and the resulting residue was dried in vacuo to give allyl (4R,5R,6S)-6-[(1R)-1-hydroxyethyl]-4-methyl-3,7-dioxo-1-azabicyclo-[3.2.0]heptane-2-carboxylate. The residue containing the compound obtained above was dissolved in anhydrous acetonitrile (10 ml) and cooled to 0°–2° C. under an atmosphere of nitrogen. To this solution were added diphenyl phosphorochloridate (0.53 ml) and N,N-diisopropyl-N-ethylamine (0.47 ml) successively and the solution was stirred at 0°–2° C. for 40 minutes. To the resulting solution were added dropwise a solution of (2S,4S)-1-allyloxycarbonyl-4-mercapto-2-[(2-ureidoethyl)oxymethyl]pyrrolidine (0.62 g) in acetonitrile (10 ml) and N,N-diisopropyl-N-ethylamine (0.38 ml) successively with stirring at 2°–5° C., and the stirring was continued at the same temperature for 2 hours. To a reaction mixture was added ethyl acetate (30 ml) and water (10 ml) with stirring, and the organic layer was separated. This layer was washed with saturated aqueous sodium chloride solution (30 ml×2), dried over magnesium sulfate and evaporated in vacuo. The residue was chromatographed on silica gel (50 g) eluting with a mixture of chloroform and methanol (9:1 V/V). The fractions containing the desired compound were collected and evaporated in vacuo to give allyl (4R,5S,6S)-3-[(2S, 4S)-1-allyloxycarbonyl-2-{(2-ureidoethyl)oxymethyl}-pyrrolidin-4-yl]thio-6-[(1R)-1-hydroxyethyl]-4-methyl-7-oxo-1-azabicyclo[3.2.0]hept-2-ene-2-carboxylate (160 mg).

IR (Neat): 1775–1760, 1690–1660 cm$^{-1}$

NMR (CDCl$_3$, δ): 1.26 (3H, d, J=7 Hz), 1.33 (3H, d, J=7 Hz), 1.70–2.15 (2H, m), 2.30–2.80 (2H, m), 4.50–4.83 (4H, m), 5.10–5.80 (4H, m), 5.70–6.20 (2H, m)

Example 3

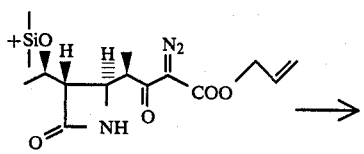

Allyl (4R,5S,6S)-3-[(2S,4S)-1-allyloxycarbonyl-2-{(2-ureidoethyl)oxymethyl}pyrrolidin-4-yl]thio-6-[(1R)-1-t-butyldimethylsilyloxyethyl]-4-methyl-7-oxo-1azabicyclo[3.2.0]hept-2-ene-2-carboxylate (0.94 g) was obtained by reacting allyl (4R)-2-diazo-4-[(2R,3S)-3-{(1R)-1-t-butyldimethylsilyloxyethyl}-4-oxoazetidin-2-yl]- 3-oxopentanoate (1.05 g) with rhodium(II) octanoate (20 mg), and then successively with diphenyl phosphorochloridate (0.58 ml) and (2S,4S)-1-allyloxycarbonyl-4-mercapto-2-[(2-ureidoethyl)oxymethyl]-pyrrolidine (1.0 g) in substantially the same manner as that of Example 1.

IR (CHCl$_3$): 1770, 1710–1650 cm$^{-1}$

NMR (CDCl$_3$, δ): 0.07 (6H,s), 0.87 (9H,s) Example 4

Example 4

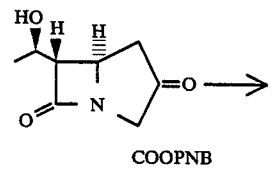

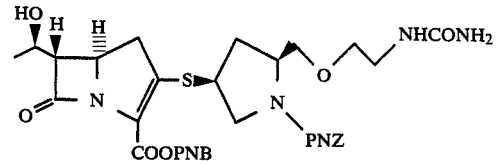

To a solution of 4-nitrobenzyl (2R,5R,6S)-6-[(1R)-1-hydroxyethyl]-3,7-dioxo-1-azabicyclo[3.2.0]heptane-2-carboxylate (0.50 g) in acetonitrile (10 ml) were added diphenyl phosphorochloridate (0.32 ml) and N,N-dissopropyl-N-ethlamine diisopropyl-N-ethylamine (0.28 ml) at −5°~0° C., and the solution was stirred at the same temperature for 30 minutes under an atmosphere of nitrogen. To the mixture were added N,N-diisopropyl-N-ethylamine (0.28 ml) and a solution of (2S,4S)-4-mercapto-1-(4-nitrobenzyloxycarbonyl)-2-[(2-ureidoethyl-)oxymethyl]pyrrolidine (0.50 g) in acetonitrile (1 ml) at −5°~0° C. The mixture was stirred at the same temperature for 30 minutes and then at ambient temperature for 2 hours. The mixture was poured into ethyl acetate (150 ml). The organic layer was washed with water (50 ml×3) and brine (50 ml) successively, dried over magnesium sulfate, and concentrated under reduced pressure to give a syrup. The syrup was crystallized from ethyl acetate to give 4-nitrobenzyl (5R,6S)-6-[(1R)-1-hydroxyethyl]-3-[(2S,4S)-1-(4-nitrobenzyloxycarbonyl)-2-{(2-ureidoethyl)oxymethyl}1-pyrrolidin-4-yl]thio-7-oxo-1-azabicyclo[3.2.0]hept-2-ene-2-carboxylate (0.51 g).

mp: 135° C. (dec.)
IR (Nujol) : 1770, 1610–1585 cm$^{-1}$
NMR (CDCl$_3$-DMSO-d$_6$, δ): 1.27 (3H, d, J=7,5 Hz)

Example 5

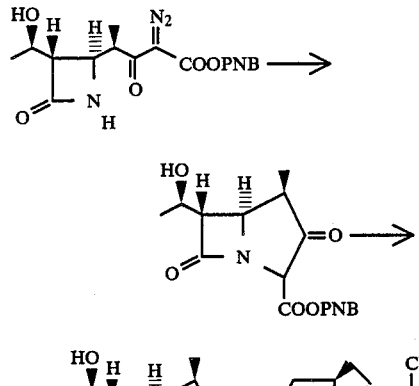

4-Nitrobenzyl (4R,5S,6S)-3-[(2S,4S)--2-(1,1-dimethyl-2-ureidoethyl)oxymethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.58 g) was obtained by reacting 4nitrobenzyl (4R)-2-diazo-4-[(2R,3S)-3-{(1R)-1-hydroxyethyl}-4-oxoazetidin-2-yl]-3-oxopentanoate (0.95 g) with (2S,4S)-2-(1,1-dimethyl-2-ureidoethyl)oxymethyl-4-mercapto-1-(4-nitrobenzyloxycarbonyl)pyrrolidine (0.93 g) in substantially the same manner as that of Example 1.

IR (Neat): 1760, 1710–1650 cm$^{-1}$
NMR (CDCl$_3$, δ): 1.1–1.4 (12H, m)

Example 6

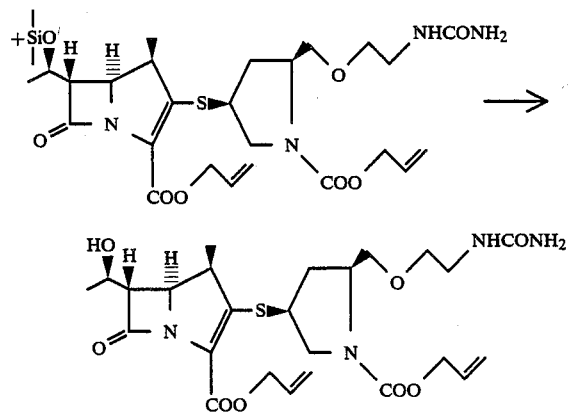

To a solution of allyl (4R,5S,6S)-3-[(2S,4S)-1-allyloxycarbonyl-2-{(2-ureidoethyl)oxymethyl}pyrrolidin-4-yl]thio-6-[(1R)-1-t-butyldimethylsilyloxyethyl]-4-methyl-7-oxo-1-azabicyclo[3.2.0]hept-2-ene-2-carboxylate (0.46 g) in tetrahydrofuran (10 ml) were added dropwise acetic acid (0.5 ml) and a 1.1 M solution (3.2 ml) of tetrabutylammonium fluoride in tetrahydrofuran at ambient temperature. The mixture was stirred at the same temperature for 26 hours. To the mixture was added ethyl acetate (100 ml) and water (100 ml). The aqueous layer was adjusted to pH 7 with saturated aqueous sodium hydrogen carbonate. The organic layer was washed with brine, dried over medium sulfate and concentrated under reduced pressure to give a syrup. The syrup was subjected to a column chromatography on silica gel (10 g) and eluted with a mixture of acetone and dichloromethane (2:1 V/V) to give allyl (4R,5S,6S)-3-[(2S,4S)-1-allyloxycarbonyl-2-{(2-ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylate (0.17 g).

IR (Neat): 1775–1760, 1690–1660 cm$^{-1}$

Example 7

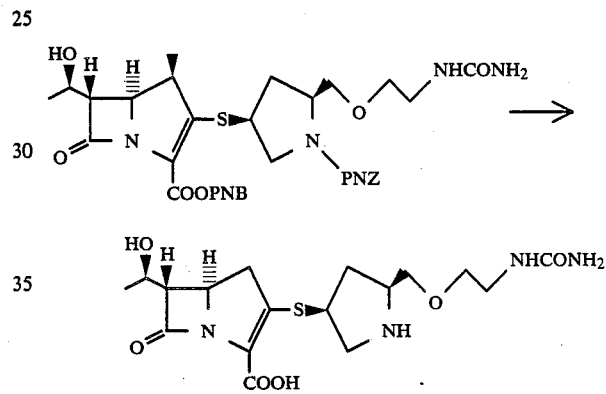

A mixture of 4-nitrobenzyl (4R,5S,6S)-6--[(1R)-1-hydroxyethyl]-4-methyl-3-[(2S,4S)-1-(4-nitrobenzyloxycarbonyl)-2-{(2-ureidoethyl)oxylmethyl}pyrrolidin-4-yl]thio-7-oxo-1-azabicyclo[3.2.0-]hept-2-ene-2-carboxylate (0.75 g), tetrahydrofuran (40 ml), 0.1M phosphate buffer (pH 6.5) (20 ml) and 20% palladium hydroxide on carbon (0.20 g) was stirred at ambient temperature for 5 hours under atmospheric pressure of hydrogen. The catalyst was removed by filtration and the filtrate was concentrated under reduced pressure to remove tetrahydrofuran. The residual solution was washed with ethyl acetate (40 ml×2) and the organic solvent was removed by evaporation. The residual solution was subjected to a column chromatography on nonionic adsorption resin "Diaion HP-20" (40 ml) eluting with a mixture of acetone and water (5:95 V/V), and lyophilized to give (4R,5S,6S)-6-[(1R)-1-hydroxyethyl]-4-methyl-7-oxo-3-[(2S,4S)-2-{(2-ureidoethyl)oxymethyl}pyrrolidin-4-yl]thio-1-azabicyclo[3.2.0]hept-2-ene-2-carboxylic acid (0.20 g).

mp: 150° C. (dec.)
IR (KBr): 1750, 1660–1550 cm$^{-1}$
NMR (D$_2$O, δ): 1.18 (3H, d, J=7 Hz), 1.26 (3H, d, J=7 Hz)
SI Mass: 429 (M+1), 369

Example 8

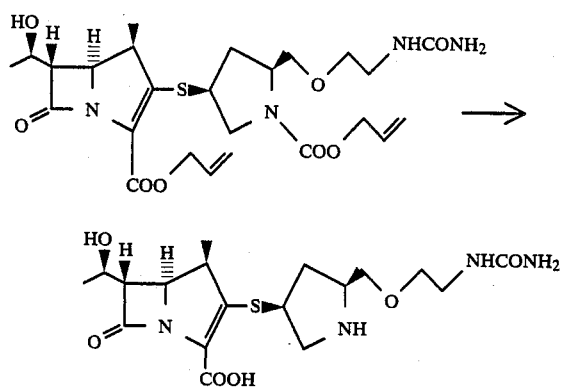

To a solution of allyl (4R,5S,6S)-3-[(2S,4S)-1-allyloxycarbonyl-2-{(2-ureidoethyl)oxymethyl}pyrrolidin-4-yl]thio-6-[(1R)-1-hydroxyethyl]-4-methyl-7-oxo-1azabicyclo[3.2.0]hept-2-ene-2-carboxylate (1.73 g) in a mixture of tetrahydrofuran (34 ml) and water (11 ml) were added triphenylphosphine (0.41 g), dimedone (1.32 g) and tetrakis(triphenylphosphine)palladium(0) (0.18 g) successively with stirring at ambient temperature. The mixture was stirred at the same temperature for 3 hours. To the solution were added ethyl acetate (50 ml) and water (30 ml). The aqueous layer was separated and washed 3 times with ethyl acetate (30 ml). This aqueous layer was concentrated in vacuo to remove the organic solvent. The residue was chromatographed on activated charcoal (made by Wako Pure Chemical Industries) (30 ml) eluting in turn with water (90 ml) and 15% aqueous isopropyl alcohol (200 ml). The fractions containing the desired compound were collected and lyophilized to give (4R,5S, 6S)-6-[(1R)-1-hydroxyethyl]-4-methyl-7-oxo-3-[(2S,4S)-2-{(2-ureidoethyl)oxymethyl}pyrrolidin-4-yl]thio-1azabicyclo[3.2.0]hept-2-ene-2-carboxylic acid (0.73 g).

IR (KBr): 1750, 1660–1550 cm$^{-1}$

This compound (513 mg) was crystallized from a mixture of ethanol (12.31 ml) and water (1.03 ml) to give colorless crystals of prism (368 mg).

mp: >182° C. (dec.)

NMR (270 MHz) (D$_2$O, δ): 1.23 (3H, d, J=7.9 Hz), 1.30 (3H, d, J=6.6 Hz), 1.81 (1H, ddd, J=5.9 Hz, J=8.2 Hz, J=14.2 Hz), 2.70 (1H, ddd, J=8.2 Hz, J=8.2 Hz, J=14.2 Hz), 3.32–3.34 (4H, m), 3.47 (1H, dd, J=2.6 Hz, J=5.9 Hz), 3.85 (1H, dd, J=3.6 Hz, J=11.2 Hz), 3.93–4.08 (2H, m), 4.24 (1H, dd, J=3.0 Hz, J=8.9 Hz), 4.27 (1H, q, J=4.3 Hz)

Example 9

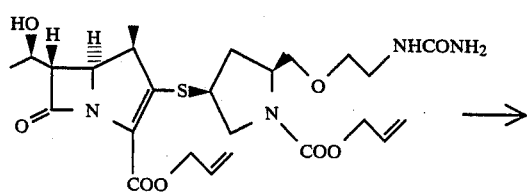

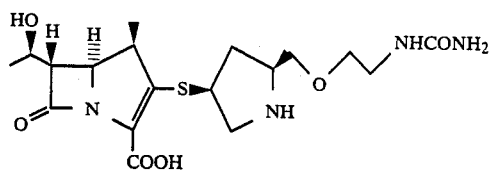

(4R,5S,6S)-6-[(1R)-1-Hydroxyethyl]-4-methyl-7-oxo-[(2S,4S)-2-{(2-ureidoethyl)oxymethyl}pyrrolidin-4-yl]thio-1-azabicyclo[3.2.0]hept-2-ene-2-carboxylic acid (249 mg) was obtained by deprotecting allyl (4R,5S,6S)-3-[(2S,4S)-1-allyloxycarbonyl-2-{(2-ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylate (500 mg) with triphenylphosphine (24 mg), tetrakis(triphenylphosphine)palladium(0) (52 mg) and morpholine (0.24 ml) which was used instead of dimedone, at 2°–5° C. in substantially the same manner as that of Example 8.

IR (KBr): 1750, 1660–1550 cm$^{-1}$

Example 10

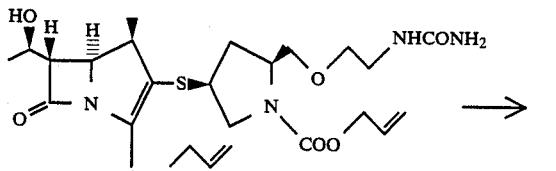

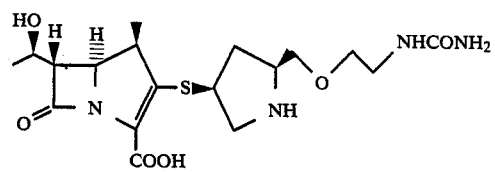

(4R,5S,6S)-6-[(1R)-1Hydroxyethyl]-4-methyl-7-oxo-3-[(2S,4S)-2-{(2-ureidoethyl)oxymethyl}pyrrolidin-4-yl]-thio-1-azabicyclo[3.2.0]hept-2-ene-2-carboxylic acid (0.29 g) was obtained by deprotecting allyl (4R,5S,6S)-3-[(2S,4S)-1-allyloxycarbonyl-2-{(2-ureidoethyl)oxymethyl}-pyrrolidin-4-yl]thio-6-[(1R)-1-hydroxyethyl]-4-methyl-7-oxo-1-azabicyclo[3.2.0]hept-2-ene-2-carboxylate (0.50 g) with triphenylphosphine (47 mg), tetrakis(triphenylphosphine)palladium(0) (52 mg), morpholine (0.24 ml) and formic acid (0.10 ml) in substantially the same manner as that of Example 8.

IR (KBr): 1750, 1660–1550 cm$^{-1}$

Example 11

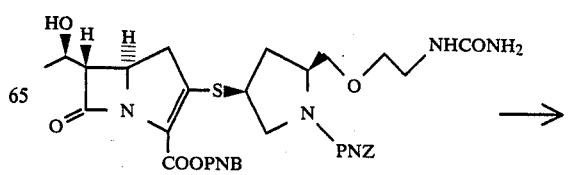

-continued

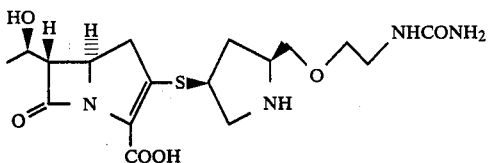

(5R,6S)-6-[(1R)-1-Hydroxyethyl]-7-oxo-3-[(2S,4S)--{(2-ureidoethyl)oxymethyl}pyrrolidin-4-yl]thio-1-azabicyclo[3.2.0]hept-2-ene-2-carboxylic acid (0.51 g) was obtained by hydrogenating 4-nitrobenzyl (5R,6S)-6-[(1R)-1-hydroxyethyl]-3-[(2S,4S)-1-(4-nitrobenzyloxycarbonyl)-2-{(2-ureidoethyl)oxymethyl}pyrrolidin-4-yl]-thio-7-oxo-1-azabicyclo[3.2.0]hept-2-ene-2-carboxylate (0.50 g) in substantially the same manner as that of Example 7.

mp: 150° C. (dec.)
IR (KBr): 1750, 1660–1540 cm$^{-1}$
NMR (CDCl$_3$, δ): 1.26 (3H, d, J=7.5 Hz)
SI MS: 415 (M$^+$+1), 398

Example 12

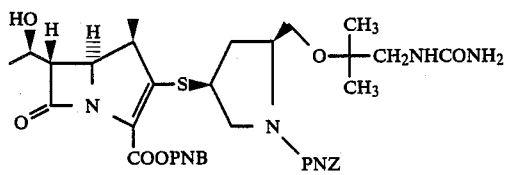

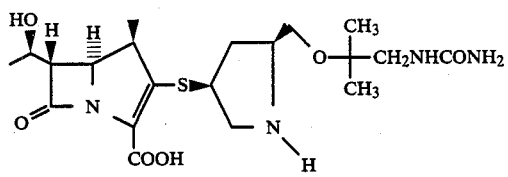

(4R,5S,6S)-3-[(2S,4S)-2-{(1,1-Dimethyl-2ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylic acid (0.21 g) was obtained by hydrogenating 4-nitrobenzyl (4R,5S,6S)-3-[(2S,4S)-2-( 1,1-dimethyl-2-ureidoethyl)oxymethyl-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (0.21 g) in substantially the same manner as that of Example 7.

mp: 190° C. (dec.)
IR (KBr): 1760–1730 cm$^{-1}$
NMR (D$_2$O, δ): 1.18–1.22 (12H, m)
SIMS: 457

Example 13

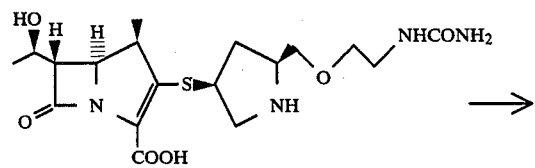

-continued

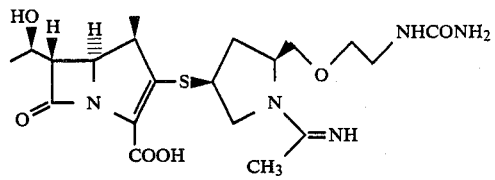

To a solution of (4R,5S,6S)-6-[(1R)-1-hydroxyethyl]-4-methyl-7-oxo-3-[(2S,4S)-2-{(2-ureidoethyl)oxymethyl}-pyrrolidin-4-yl]thio-1-azabicyclo[3.2.0]hept-2-ene-2-carboxylic acid (0.15 g) in water (30 ml) was added ethyl acetimidate hydrochloride (1.65 g) by portions at 0°–5° C., keeping the pH between 8.4–8.6 with 10% aqueous potassium carbonate. After adjusting to pH 6.5 with 1N aqueous hydrochloric acid, the solution was washed with 10% solution of tetrahydrofuran in ethyl acetate (50 ml) by four portions and the organic solvent was removed by evaporation. The residual solution was subjected to a column chromatography on nonionic adsorption resin, "HP-20" (30 ml), washed with water, eluted with 5% aqueous isopropyl alcohol and lyophilized to give (4R,5S,6S)-3-[(2S,4S)-1-acetimidoyl-2-{(2-ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylic acid (0.11 g).

IR (KBr): 1800–1710 cm$^{-1}$
NMR (D$_2$O, δ): 1.27 (6H, t, J=7.4 Hz), 2.30 and 2.38 (total 3H, each s)
SIMS: 470 (M$^+$), 453 (M$^+$−17), 427 (M$^+$−43)

What we claim is:

1. A compound of the formula:

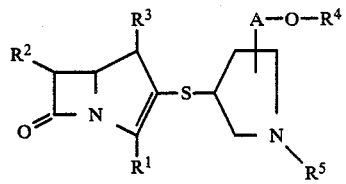

in which
R$^1$ is carboxy or esterified carboxy,
R$^2$ is hydroxy(lower)alkyl, lower alkenyloxycarbonyloxy(lower)alkyl, phenyl(lower)alkoxy carbonyloxy(lower)alkyl, nitrophenyl(lower)alkoxycarbonyloxy(lower)alkyl, mono- or di- or triphenyl(lower)alkenyloxy(lower)alkyl, tri(lower)alkylsilyloxy(lower)alkyl, triphenylsilyloxy(lower)alkyl or tribenzylsilyloxy(lower)alkyl,
R$^3$ is hydrogen or lower alkyl,
R$^4$ is mono(or di or tri)phenyl(lower)alkylureido(lower)alkyl, mono(or di)(lower)alkoxyphenyl(lower)alkylureido(lower)alkyl, bis(lower alkoxyphenyl)(lower)alkylureido(lower)alkyl or ureido(lower)alkyl,
R$^5$ is hydrogen, lower alkanimidoyl lower alkenyloxycarbonyl, phenyl(lower)alkoxycarbonyl or nitrophenyl(lower)alkoxycarbonyl, and
A is lower alkylene,
or pharmaceutically acceptable salts thereof.

2. A compound of claim 1, wherein
R$^1$ is carboxy,
R$^2$ is hydroxy(C$_1$–C$_4$)alkyl,
R$^3$ is hydrogen or C$_1$–C$_4$ alkyl,
R$^4$ is ureido(C$_1$–C$_4$)alkyl, $R^5$ is hydrogen or $(C_1-C_4)$alkanimidoyl, and
A is $C_1-C_4$ alkylene.

3. A compound of claim 2, wherein
$R^3$ is $C_1-C_4$ alkyl.

4. A compound of claim 3, wherein
$R^2$ is 1-hydroxyethyl,
$R^3$ is methyl,
$R^4$ is 2-ureidoethyl or 1,1-dimethyl-2-ureidoethyl,
$R^5$ is hydrogen or acetimidoyl, and
A is methylene.

5. A compound of claim 4, which is (4R,5S,6S)-6-[(1R)-1-hydroxyethyl]-4-methyl-7-oxo-3-[(2S,4S)-2-{(2-ureidoethyl)oxymethyl}-pyrrolidin-4-yl]thio-1-azabicyclo[3.2.0]hept-2-ene-2-carboxylic acid.

6. A compound of claim 4, which is (4R,5S,6S)-3-[(2S,4S)-2-{(1,1-dimethyl-2-ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylic acid.

7. A compound of claim 4, which is (4R,5S,6S)-3-[(2S,4S)-1-acetimidoyl-2-{(2-ureidoethyl)oxymethyl}pyrrolidin-4-yl]thio-6-[(1R)-1-hydroxyethyl]-4-methyl-7-oxo-1-azabicyclo[3.2.0]hept-2-ene-2-carboxylic acid.

8. A compound of claim 2, wherein
$R^3$ is hydrogen.

9. A compound of claim 8, wherein
$R^2$ is 1-hydroxyethyl,
$R^4$ is 2-ureidoethyl or 1,1-dimethyl-2-ureidoethyl,
$R^5$ is hydrogen, and
A is methylene.

10. A compound of claim 9, which is (5R,6S)-6-[(1R)-1-hydroxyethyl]-7-oxo-3-[(2S,4S)-2-{(2-ureidoethyl)oxymethyl}pyrrolidin-4-yl]thio-1-azabicyclo[3.2.0]hept-2-ene-2-carboxylic acid.

11. An antimicrobial pharmaceutical composition comprising an antimicrobially effective amount of a compound of claim 1, in admixture with a pharmaceutically acceptable carrier or excipient.

12. An antimicrobial method for the treatment of infectious diseases which comprises administering an antimicorbially effective amount of a compound of claim 1 to a human being or animal.

* * * * *

UNITED STATES PATENT AND TRADEMARK OFFICE
CERTIFICATE OF CORRECTION

PATENT NO. : 4,822,787

DATED : April 18, 1989

INVENTOR(S) : MASAYOSHI MURATA ET AL

It is certified that error appears in the above-identified patent and that said Letters Patent is hereby corrected as shown below:

In Column 33, line 5, the formula:

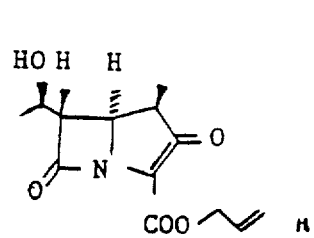

should read:

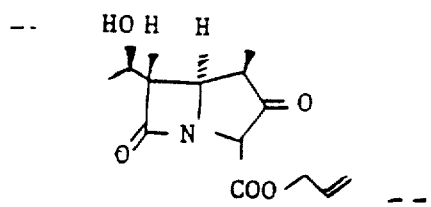

UNITED STATES PATENT AND TRADEMARK OFFICE
CERTIFICATE OF CORRECTION

PATENT NO. : 4,822,787
DATED : April 18, 1989
INVENTOR(S) : MASAYOSHI MURATA ET AL It is certified that error appears in the above-identified patent and that said Letters Patent is hereby corrected as shown below:

Column 34, lines 21 and 22, "allyloxycarb onyl" should read -- allyloxycar-bonyl--.

Column 34, line 40, the formula:

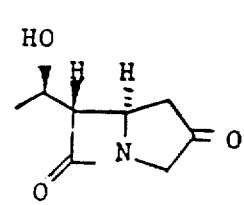

should read:

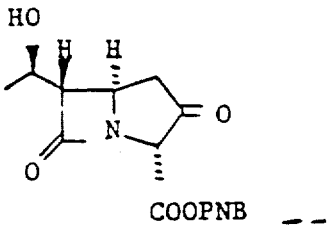

UNITED STATES PATENT AND TRADEMARK OFFICE
CERTIFICATE OF CORRECTION

PATENT NO. : 4,822,787
DATED : April 18, 1989
INVENTOR(S) : MASAYOSHI MURATA ET AL It is certified that error appears in the above-identified patent and that said Letters Patent is hereby corrected as shown below:

Column 40, line 47, "phenyl(lower)alkoxy car-"

should read --phenyl(lower)alkoxycar- -- line 50, "phenyl(lower)alkenyloxy(lower)alkyl"

should read --phenyl(lower)alkyloxy(lower)alkyl-- line 59, "alkanimidoyl" should read

--alkanimidoyl,--

Column 42, line 20, "antimicorbially" should read

--antimicrobially--

Signed and Sealed this

Seventeenth Day of July, 1990

*Attest:*

HARRY F. MANBECK, JR.

*Attesting Officer*  *Commissioner of Patents and Trademarks*